United States Patent
Vilain et al.

(10) Patent No.: US 10,435,743 B2
(45) Date of Patent: Oct. 8, 2019

(54) METHOD TO ESTIMATE AGE OF INDIVIDUAL BASED ON EPIGENETIC MARKERS IN BIOLOGICAL SAMPLE

(75) Inventors: Eric Vilain, Los Angeles, CA (US); Sven Bocklandt, Los Angeles, CA (US); Steve Horvath, Los Angeles, CA (US); Janet Sinsheimer, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 812 days.

(21) Appl. No.: 14/119,145

(22) PCT Filed: May 18, 2012

(86) PCT No.: PCT/US2012/038552
§ 371 (c)(1),
(2), (4) Date: Feb. 28, 2014

(87) PCT Pub. No.: WO2012/162139
PCT Pub. Date: Nov. 29, 2012

(65) Prior Publication Data
US 2014/0228231 A1   Aug. 14, 2014

Related U.S. Application Data

(60) Provisional application No. 61/488,277, filed on May 20, 2011.

(51) Int. Cl.
*C12Q 1/68* (2018.01)
*C12Q 1/6876* (2018.01)
*C12Q 1/6883* (2018.01)

(52) U.S. Cl.
CPC ......... *C12Q 1/6876* (2013.01); *C12Q 1/6883* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,333,675 A | 8/1994 | Mullis et al. |
| 5,576,180 A | 11/1996 | Melancon et al. |
| 5,744,305 A | 4/1998 | Fodor et al. |
| 5,786,146 A | 7/1998 | Herman et al. |
| 5,912,147 A | 6/1999 | Stoler et al. |
| 6,017,704 A | 1/2000 | Herman et al. |
| 6,200,756 B1 | 3/2001 | Herman et al. |
| 6,214,556 B1 | 4/2001 | Olek et al. |
| 6,251,592 B1 | 6/2001 | Tang et al. |
| 6,251,594 B1 | 6/2001 | Gonzalgo et al. |
| 6,265,171 B1 | 7/2001 | Herman et al. |
| 6,287,778 B1 | 9/2001 | Huang et al. |
| 6,300,070 B1 | 10/2001 | Boles et al. |
| 6,300,071 B1 | 10/2001 | Vuylsteke et al. |
| 6,331,393 B1 | 12/2001 | Laird et al. |
| 6,582,908 B2 | 6/2003 | Fodor et al. |
| 6,605,432 B1 | 8/2003 | Huang |
| 6,929,914 B2 | 8/2005 | Myrick |
| 7,238,486 B2 | 7/2007 | Pourmand et al. |
| 7,501,253 B2 | 3/2009 | Pourmand et al. |
| 7,700,324 B1 | 4/2010 | Issa et al. |
| 2003/0143606 A1 | 7/2003 | Olek et al. |
| 2003/0148326 A1 | 8/2003 | Olek et al. |
| 2003/0148327 A1 | 8/2003 | Olek et al. |
| 2004/0132026 A1 | 7/2004 | Olek |
| 2005/0009059 A1 | 1/2005 | Shapero et al. |
| 2005/0196792 A1 | 9/2005 | Fodor et al. |
| 2006/0292585 A1 | 12/2006 | Nautiyal et al. |
| 2009/0263804 A1 | 10/2009 | Landfield et al. |

FOREIGN PATENT DOCUMENTS

| WO | 03025215 | 3/2003 |
|---|---|---|
| WO | 2004096825 A1 | 11/2004 |

OTHER PUBLICATIONS

Bibikova et al. (2009) Chapter 12 Goldengate assay for DNA methylation profiling on p. 149-163 in Book: DNA methylation: methods and Protocols edited by Jorg Tost in second edition vol. 507.*
Hernandez et al. (2011 advance access publication date Jan. 7, 2011) Human Molecular Genetics vol. 20 No. 6 pp. 1164-1172. doi:10. 1093/hmg/ddq561.*
Rakyan et al. (Genome Research, 2010, 20(4):434-439).*
Hewakapuge et al. (Thesis: "Prediction of age from DNA", Oct. 2009, p. 1-179, Victoria University).*
Deneberg et al. (Leukemia, 2010, vol. 24, p. 932-941).*
Adkins et al. (BMC Medical Genetics, 2011, vol. 12, p. 47-59).*
Teschendorff et al. (Genome Research, 20: 440-446).*
Koch et al. (Aging, 2011, 3(10):1-10).*
Sproul et al. (PNAS, 2011, 108(11):4364-4369).*
Houshdaran et al. (PLos ONE, 2007, issue 12, e1289:p. 1-9).*
Bell et al. "Epigenome-Wide scans identify differentially methylated regions for age and age-related phenotypes in a healthy ageing population", Plos Genetics, vol. 8, No. 4, 2012.

(Continued)

*Primary Examiner* — Stephanie K Mummert
(74) *Attorney, Agent, or Firm* — Gates & Cooper LLP

(57) ABSTRACT

The invention provides methods and materials that use observation of DNA characteristics to obtain information relating to the age of individuals. The instant disclosure identifies 88 sites in or near 80 genes for which the degree of cytosine methylation in epithelial and/or white blood cells is significantly correlated with age. In illustrative embodiments of the invention, cytosine methylation patterns the promoters of the EDARADD, TOMIL1, and NPTX2 genes are used to predict the age of an individual with a high degree of accuracy.

18 Claims, 15 Drawing Sheets
Specification includes a Sequence Listing.

(56) References Cited

OTHER PUBLICATIONS

Hannum et al. "Genome-wide methylation profiles reveal quantitative views of human aging rates", Molecular Cell, vol. 49, No. 2, pp. 359-367, 2013.

Ben-Avraham et al. "Epigenetic genome-wide association methylation in aging and longevity", Epigenomics, vol. 4, No. 5, pp. 503-509, 2012.

Nazor et al. "Recurrent variations in DNA methylation in human pulripotent stem cells and their differentiated derivatives", Cell Stem Cell, vol. 10, No. 5, pp. 620-634, 2012.

PCT Invitation to Pay Additional Fees with Annex to Form PCT/ISA/206 Communication Relating to the Results of the Partial International Search for PCT/US2014/058089.

Berdasco et al., "Hot topics in epigenetic mechanisms of aging: 2011." Aging cell 11.2 (2012): 181-186.

Bestor, "The DNA methyltransferases of mammals." Human molecular genetics 9.16 (2000): 2395-2402.

Bocklandt et al. "Epigenetic predictor of age." PloS one 6.6 (2011): e14821.

Boks et al., "The relationship of DNA methylation with age, gender and genotype in twins and healthy controls." PloS one 4.8 (2009): e6767.

Bork et al., "DNA methylation pattern changes upon long-term culture and aging of human mesenchymal stromal cells." Aging cell 9.1 (2010): 54-63.

Fraga et al., "Epigenetic differences arise during the lifetime of monozygotic twins." Proceedings of the National Academy of Sciences of the United States of America 102.30 (2005): 10604-10609.

Grönniger et al., "Aging and chronic sun exposure cause distinct epigenetic changes in human skin." PLoS genetics 6.5 (2010): e1000971.

Horvath et al., "Geometric interpretation of gene coexpression network analysis." PLoS computational biology 4.8 (2008): e1000117.

Kanehisa, "Use of statistical criteria for screening potential homologies in nucleic acid sequences." Nucleic acids research 12.1Part1 (1984): 203-213.

Koch et al. "Epigenetic-aging-signature to determine age in different tissues." Aging (Albany NY) 3.10 (2011): 1018-1027.

Langfelder et al., "WGCNA: an R package for weighted correlation network analysis." BMC bioinformatics 9.1 (2008): 559.

Maegawa et al., "Widespread and tissue specific age-related DNA methylation changes in mice." Genome Research 20.3 (2010): 332-340.

Marks et al., "Dimethyl sulfoxide to vorinostat: development of this histone deacetylase inhibitor as an anticancer drug." Nature biotechnology 25.1 (2007): 84-90.

Oakeley, "DNA methylation analysis: a review of current methodologies." Pharmacology & therapeutics 84.3 (1999): 389-400.

Olek et al., "A modified and improved method for bisulphite based cytosine methylation analysis." Nucleic acids research 24.24 (1996): 5064-5066.

Rakyan et al. "Human aging-associated DNA hypermethylation occurs preferentially at bivalent chromatin domains." Genome research 20.4 (2010): 434-439.

Syvänen, "Accessing genetic variation: genotyping single nucleotide polymorphisms." Nature Reviews Genetics 2.12 (2001): 930-942.

Teschendorff et al., "Age-dependent DNA methylation of genes that are suppressed in stem cells is a hallmark of cancer." Genome research 20.4 (2010): 440-446.

Tibshirani, "The lasso method for variable selection in the Cox model." Statistics in medicine 16.4 (1997): 385-395.

Wang et al., "Age-specific epigenetic drift in late-onset Alzheimer's disease." PLoS One 3.7 (2008): e2698.

Wu et al., "Genome-wide association analysis by lasso penalized logistic regression." Bioinformatics 25.6 (2009): 714-721.

Zhang et al., "A general framework for weighted gene co-expression network analysis." Statistical applications in genetics and molecular biology 4.1 (2005): 1128.

PCT International Search Report and Written Opinion dated Sep. 20, 2012 for PCT Application No. PCT/US2012/038552.

De Magalhaes, Joao Pedro, et al., "Meta-analysis of age-related gene expression profiles identifies common signatures of aging", Bioinformatics, 2009, pp. 875-881, vol. 25, Issue No. 7.

Danabase GenBank, GX282377, Dec. 12, 2010.

Hernandez, Dena G., et al., "Distinct DNA methylation changes highly correlated with chronological age in the human brain", Human Molecular Genetics, 2011, pp. 1164-1172, vol. 20, Issue No. 6.

* cited by examiner

FIG. 4A

| TargetID | Chr | Gene_ID | Symbol | r | p-value | q-value |
|---|---|---|---|---|---|---|
| cg27553955 | 2 | 170850 | KCNG3 | 0.807 | 8.38E-09 | 0.00012 |
| cg12799895 | 7 | 4885 | NPTX2 | 0.754 | 2.59E-07 | 0.00124 |
| cg21296230 | 15 | 26585 | GREM1 | 0.758 | 2.14E-07 | 0.00124 |
| cg04084157 | 7 | 7425 | VGF | 0.726 | 1.20E-06 | 0.00188 |
| cg25148589 | 4 | 2891 | GRIA2 | 0.723 | 1.37E-06 | 0.00188 |
| cg17861230 | 19 | 5143 | PDE4C | 0.734 | 8.00E-07 | 0.00188 |
| cg03734874 | 14 | 388021 | FLJ42486 | 0.728 | 1.07E-06 | 0.00188 |
| cg18236477 | 13 | 51761 | ATP8A2 | 0.722 | 1.45E-06 | 0.00188 |
| cg27320127 | 2 | 56660 | KCNK12 | 0.722 | 1.44E-06 | 0.00188 |
| cg07621046 | 10 | 143379 | C10orf82 | 0.724 | 1.30E-06 | 0.00188 |
| cg14456683 | 3 | 7545 | ZIC1 | 0.709 | 2.71E-06 | 0.00277 |
| cg21801378 | 15 | 60677 | BRUNOL6 | 0.703 | 3.51E-06 | 0.00291 |
| cg00107187 | 14 | 388021 | FLJ42486 | 0.702 | 3.65E-06 | 0.00291 |
| cg05508084 | 19 | 63934 | ZNF667 | 0.704 | 3.37E-06 | 0.00291 |
| cg07533148 | 1 | 25893 | TRIM58 | 0.701 | 3.89E-06 | 0.00291 |
| cg03975694 | 19 | 163255 | ZNF540 | 0.700 | 4.06E-06 | 0.00291 |
| cg19945840 | 1 | 126792 | B3GALT6 | 0.699 | 4.30E-06 | 0.00293 |

FIG. 4B

| | | | | | | |
|---|---|---|---|---|---|---|
| cg00399483 | 18 | 1630 | DCC | 0.697 | 4.62E-06 | 0.00301 |
| cg06291867 | 10 | 3363 | HTR7 | 0.687 | 7.32E-06 | 0.00438 |
| cg24826867 | 16 | 3394 | IRF8 | 0.681 | 9.24E-06 | 0.00474 |
| cg06092815 | 2 | 80309 | SKIP | 0.679 | 1.02E-05 | 0.00503 |
| cg19885761 | 5 | 10814 | CPLX2 | 0.677 | 1.10E-05 | 0.00526 |
| cg24199834 | 4 | 5458 | POU4F2 | 0.675 | 1.21E-05 | 0.00561 |
| cg04528819 | 7 | 136259 | KLF14 | 0.673 | 1.29E-05 | 0.00578 |
| cg13434842 | 8 | 2626 | GATA4 | 0.667 | 1.64E-05 | 0.00711 |
| cg02008154 | 7 | 57057 | TBX20 | 0.664 | 1.86E-05 | 0.00786 |
| cg25044651 | 5 | 206338 | FLJ90650 | 0.661 | 2.05E-05 | 0.00803 |
| cg02994956 | 22 | 4744 | NEFH | 0.661 | 2.07E-05 | 0.00803 |
| cg20366906 | 13 | 5100 | PCDH8 | 0.656 | 2.50E-05 | 0.00944 |
| cg27389185 | 19 | 163255 | ZNF540 | 0.654 | 2.73E-05 | 0.01003 |
| cg14826456 | 10 | 153 | ADRB1 | 0.653 | 2.88E-05 | 0.01032 |
| cg12111714 | 13 | 51761 | ATP8A2 | 0.651 | 3.03E-05 | 0.01061 |
| cg12457773 | 6 | 140767 | VMP | 0.649 | 3.36E-05 | 0.01147 |
| cg11981599 | 8 | 2626 | GATA4 | 0.646 | 3.67E-05 | 0.01166 |
| cg00059225 | 5 | 2741 | GLRA1 | 0.646 | 3.63E-05 | 0.01166 |

FIG. 4C

| | | | | | | |
|---|---|---|---|---|---|---|
| cg06572160 | 19 | 3748 | KCNC3 | 0.642 | 4.21E-05 | 0.01262 |
| cg08668790 | 19 | 7710 | ZNF154 | 0.642 | 4.22E-05 | 0.01262 |
| cg12782180 | 7 | 3952 | LEP | 0.641 | 4.43E-05 | 0.01296 |
| cg20134215 | 6 | 84539 | MCHR2 | 0.633 | 5.84E-05 | 0.01505 |
| cg13921352 | 3 | 151647 | FAM19A4 | 0.631 | 6.37E-05 | 0.01575 |
| cg13614181 | 13 | 28984 | RGC32 | 0.628 | 6.89E-05 | 0.01648 |
| cg23563234 | 5 | 56099 | PCDHGB7 | 0.628 | 7.06E-05 | 0.01661 |
| cg00201234 | 3 | 2199 | FBLN2 | 0.626 | 7.57E-05 | 0.01696 |
| cg21992250 | 11 | 51296 | SLC15A3 | 0.626 | 7.56E-05 | 0.01696 |
| cg00911351 | 5 | 8641 | PCDHGB4 | 0.625 | 7.73E-05 | 0.01705 |
| cg19594666 | 7 | 3952 | LEP | 0.624 | 7.91E-05 | 0.01720 |
| cg15425280 | 4 | 2891 | GRIA2 | 0.619 | 9.39E-05 | 0.01898 |
| cg06156376 | 3 | 6474 | SHOX2 | 0.619 | 9.37E-05 | 0.01898 |
| cg19831077 | 7 | 349136 | LOC349136 | 0.618 | 9.77E-05 | 0.01946 |
| cg27409364 | 11 | 3746 | KCNC1 | 0.613 | 0.00011468 | 0.02137 |
| cg15747595 | 8 | 85453 | TSPYL5 | 0.612 | 0.000121753 | 0.02211 |
| cg02154186 | 8 | 10687 | PNMA2 | 0.608 | 0.000135948 | 0.02408 |
| cg20616414 | 9 | 65268 | WNK2 | 0.605 | 0.000148266 | 0.02502 |

FIG. 4D

| | | | | | | |
|---|---|---|---|---|---|---|
| cg10235817 | 4 | 152 | ADRA2C | 0.605 | 0.000151453 | 0.02526 |
| cg16232126 | 2 | 60482 | SLC5A7 | 0.602 | 0.00016384 | 0.02671 |
| cg24646414 | 8 | 2626 | GATA4 | 0.603 | 0.000162296 | 0.02671 |
| cg17241310 | 1 | 343472 | BARHL2 | 0.600 | 0.00017402 | 0.02750 |
| cg10031651 | 3 | 79442 | LRRC2 | 0.596 | 0.000199077 | 0.03104 |
| cg23290344 | 8 | 4741 | NEF3 | 0.595 | 0.000207878 | 0.03207 |
| cg06908778 | 10 | 9576 | SPAG6 | 0.591 | 0.000230493 | 0.03283 |
| cg02844545 | 6 | 9247 | GCM2 | 0.594 | 0.000215307 | 0.03283 |
| cg14614211 | 10 | 283078 | IRXL1 | 0.592 | 0.000224639 | 0.03283 |
| cg25511429 | 6 | 51299 | NRN1 | 0.589 | 0.000244086 | 0.03367 |
| cg15201635 | 16 | 55512 | SMPD3 | 0.590 | 0.000243284 | 0.03367 |
| cg19246110 | 19 | 79891 | ZNF671 | 0.589 | 0.000251007 | 0.03397 |
| cg06760035 | 17 | 3214 | HOXB4 | 0.587 | 0.000263627 | 0.03534 |
| cg13603171 | 6 | 26002 | MOXD1 | 0.583 | 0.000295067 | 0.03883 |
| cg13282837 | 14 | 8115 | TCL1A | 0.579 | 0.00033117 | 0.04280 |
| cg20792062 | 12 | 3741 | KCNA5 | 0.571 | 0.000421691 | 0.04999 |
| cg02228185 | 17 | 443 | ASPA | -0.731 | 9.14E-07 | 0.00188 |
| cg13547237 | 11 | 83638 | Bles03 | -0.717 | 1.84E-06 | 0.00218 |

FIG. 4E

| | | | | | | |
|---|---|---|---|---|---|---|
| cg09809672 | 1 | 128178 | EDARADD | -0.715 | 1.98E-06 | 0.00218 |
| cg01293143 | 20 | 6919 | TCEA2 | -0.703 | 3.61E-06 | 0.00291 |
| cg05822532 | 7 | 2006 | ELN | -0.688 | 7.00E-06 | 0.00437 |
| cg07408456 | 19 | 114770 | PGLYRP2 | -0.685 | 7.90E-06 | 0.00453 |
| cg08468689 | 17 | 84514 | LGP1 | -0.682 | 8.74E-06 | 0.00464 |
| cg27210390 | 17 | 10040 | TOM1L1 | -0.683 | 8.53E-06 | 0.00464 |
| cg01820374 | 12 | 3902 | LAG3 | -0.663 | 1.93E-05 | 0.00790 |
| cg17589341 | 18 | 6563 | SLC14A1 | -0.640 | 4.63E-05 | 0.01302 |
| cg19761273 | 17 | 1453 | CSNK1D | -0.634 | 5.62E-05 | 0.01493 |
| cg03440846 | 20 | 55902 | ACSS2 | -0.611 | 0.00012427 | 0.02228 |
| cg08909157 | 9 | 157983 | C9orf66 | -0.607 | 0.00013896 | 0.02431 |
| cg11136562 | 5 | 64411 | CENTD3 | -0.592 | 0.000227926 | 0.03283 |
| cg16464322 | 19 | 3191 | HNRPL | -0.592 | 0.000227715 | 0.03283 |
| cg08872742 | 16 | 1003 | CDH5 | -0.582 | 0.00030785 | 0.04015 |
| cg18328933 | 3 | 25864 | ABHD14A | -0.579 | 0.000338098 | 0.04330 |
| cg15784615 | 12 | 4055 | LTBR | -0.577 | 0.000350304 | 0.04374 |
| cg23282949 | X | 5973 | RENBP | -0.577 | 0.000358602 | 0.04435 |

| TargetID | Chr | MapInfo | Gene_ID | Symbol | corr | qval |
|---|---|---|---|---|---|---|
| cg00059225 | 5 | 151284550 | 2741 | GLRA1 | 0.646 | 0.012 |
| cg12799895 | 7 | 98084588 | 4885 | NPTX2 | 0.754 | 0.001 |
| cg15747595 | 8 | 98359056 | 85453 | TSPYL5 | 0.612 | 0.022 |
| cg16232126 | 2 | 107969437 | 60482 | SLC5A7 | 0.602 | 0.027 |
| cg18236477 | 13 | 24941066 | 51761 | ATP8A2 | 0.722 | 0.002 |
| cg19594666 | 7 | 127668516 | 3952 | LEP | 0.624 | 0.017 |
| cg19885761 | 5 | 175156252 | 10814 | CPLX2 | 0.677 | 0.005 |
| cg19945840 | 1 | 1157899 | 126792 | B3GALT6 | 0.699 | 0.003 |
| cg21801378 | 15 | 70399179 | 60677 | BRUNOL6 | 0.703 | 0.003 |
| cg27320127 | 2 | 47651900 | 56660 | KCNK12 | 0.722 | 0.002 |

FIG. 5

| Category | Significance | List of genes in each category |
|---|---|---|
| Cardiovascular disease | $p=1.59 \times 10^{-6}$ | ADRA2C, ADRB1, ATP8A2, DCC, ELN, FAM19A4, GATA4, GRIA2, HTR7, IRF8, KCNA5, KCNC1, LEP, MOXD1, NRSN1, PDE4C, TBX20 |
| Genetic disease | $p=1.59 \times 10^{-6}$ | ADRA2C, ADRB1, ASPA, ATP8A2, CPLX2, EDARADD, ELN, GATA4, GCM2, GRIA2, HTR7, KCNA5, LEP, NEFH, NEFM, PCDH8, PDE4C, SLC14A1, SLC5A7, TBX20 |
| Neurological disease | $p=1.47 \times 10^{-4}$ | ADRA2C, ADRB1, ASPA, ATP8A2, CPLX2, GRIA2, HTR7, LEP, NEFH, NEFM, PCDH8, PDE4C, SLC14A1, SLC5A7 |
| Molecular transport | $p=2.4 \times 10^{-3}$ | ADRB1, CPLX2, GLRA1, HTR7, KCNA5, KCNC1, KCNC3, LEP, SLC14A1, SLC5A7 |

FIG. 6

METHOD TO ESTIMATE AGE OF INDIVIDUAL BASED ON EPIGENETIC MARKERS IN BIOLOGICAL SAMPLE

REFERENCE TO RELATED APPLICATIONS

This application claims priority under Section 119(e) from U.S. Provisional Application Ser. No. 61/488,277, filed May 20, 2011, the contents of which are incorporated herein by reference.

BACKGROUND OF THE INVENTION

1. Field of the Invention

This invention relates to methods of detecting and analyzing patterns of cytosine methylation in genomic DNA.

2. Description of Related Art

Throughout development, cells and tissues differentiate and change as an organism ages. These changes include alterations to telomeres, accumulation of DNA mutations, decay of cellular and organ structures, and changes in gene expression (see, e.g. Goyns M H (2002) *Mech Ageing Dev* 123: 791-799). Both differentiation of tissues and aging effects are at least partially caused by chemical modifications of the genome, such as DNA methylation. In particular, the genomic DNA of higher eukaryotes contains modified nucleosides including 5-methyl cytosines. This modification is usually found as part of the dinucleotide CpG.

DNA methylation is an epigenetic determinant of gene expression. Patterns of CpG methylation are heritable, tissue specific, and correlate with gene expression. The consequence of methylation is usually gene silencing. DNA methylation also correlates with other cellular processes including embryonic development, chromatin structure, genomic imprinting, somatic X-chromosome inactivation in females, inhibition of transcription and transposition of foreign DNA and timing of DNA replication. When a gene is highly methylated it is less likely to be expressed. Thus the identification of sites in the genome containing 5-meC is important in understanding cell-type specific programs of gene expression and how gene expression profiles are altered during both normal development and diseases such as cancer. Mapping of DNA methylation patterns is important for understanding diverse biological processes such as the regulation of imprinted genes, X chromosome inactivation, and tumor suppressor gene silencing in human cancers.

Several studies have investigated the epigenetic state of a small number of selected genes or CpG islands in subjects of varying age or have measured the global changes in DNA methylation with increasing age (see, e.g. Boks M P, et al. (2009) *PLoS One* 4: e6767; and Fraga M F, et al. (2005) *Proc Natl Acad Sci USA* 102: 10604-10609). Recently, unbiased genome-wide studies have documented age effects on DNA methylation in cultured cells, mice, and humans (see, e.g. see, e.g. Bork S, et al. (2009) *Aging Cell* 9: 54-63; Maegawa S, et al. (2010) *Genome Res* 20: 332-340; and Teschendorff A E, et al. (2010) *Genome Res* 20: 440-446; Gronniger E, et al. (2010) *PLoS Genet* 6: e1000971; Rakyan V K, et al. (2010) *Genome Res* 20: 434-439). In these reports, the subject's were of a limited age range, and the continuity of the age related changes was not defined. Consequently, estimating the age of an individual by observing methylation patterns in their genomic DNA has not been possible.

Methods for estimating the age of an individual by observing methylation patterns in genomic DNA obtained from a biological sample have a number of applications. For example, the characterization of biological materials is one of the most important methods for identification of individuals in forensic medicine and/or in criminal investigations (see, e.g. van Oorschot et al., Investigative Genetics 2010, 1:14; and Thompson et al., Methods Mol Biol. 2012; 830: 3-16). When analyzing biological materials found at a crime scene, common procedures include DNA analysis techniques such as DNA fingerprinting to specifically identify the individual from which the biological material was derived. New DNA analysis techniques, for example those that can be used to predict an approximate age of an individual, are desirable.

SUMMARY OF THE INVENTION

As noted above, the genetic material in individuals is observed to change as they age. The disclosure provided herein includes experiments examining such changes by measuring patterns of DNA methylation in a population of individuals ranging in age from 18 to 70. These experiments identified 88 specific regions within human genomic DNA where the amount of DNA methylation correlates with the age of the individual. The invention disclosed herein includes methodologies where an amount of DNA methylation can be correlated with a predicted age. In certain working embodiments of the invention, the average absolute difference between a predicted age and actual age was 3.5 years. Some embodiments of the invention can be used, for example, by forensic scientists to estimate the age of an individual from a biological sample found at a crime scene. Other embodiments of the invention can also be used by medical personnel to assess, for example, an individual's risk for one or more age related pathologies.

The invention disclosed herein has a number of embodiments. One embodiment of the invention is a method of obtaining information useful to predict an age of an individual by observing the methylation status of one or more specific loci in the genomic DNA. Such embodiments comprise the steps of obtaining genomic DNA from white blood cells or epithelial cells derived from the individual; and then observing cytosine methylation of one or more (and typically two, three, four or more) CG loci in the genomic DNA selected from the group consisting of CG locus designation: cg27553955, cg12799895, cg21296230, cg04084157, cg25148589, cg17861230, cg03734874, cg18236477, cg27320127, cg07621046, cg14456683, cg21801378, cg00107187, cg05508084, cg07533148, cg03975694, cg19945840, cg00399483, cg06291867, cg24826867, cg06092815, cg19885761, cg24199834, cg04528819, cg13434842, cg02008154, cg25044651, cg02994956, cg20366906, cg27389185, cg14826456, cg12111714, cg12457773, cg11981599, cg00059225, cg06572160, cg08668790, cg12782180, cg20134215, cg13921352, cg13614181, cg23563234, cg00201234, cg21992250, cg00911351, cg19594666, cg15425280, cg06156376, cg19831077, cg27409364, cg15747595, cg02154186, cg20616414, cg10235817, cg16232126, cg24646414, cg17241310, cg10031651, cg23290344, cg06908778, cg02844545, cg14614211, cg25511429, cg15201635, cg19246110, cg06760035, cg13603171, cg13282837, cg20792062, cg02228185, cg13547237, cg09809672, cg01293143, cg05822532, cg07408456, cg08468689, cg27210390, cg01820374, cg17589341, cg19761273, cg03440846, cg08909157, cg11136562, cg16464322, cg08872742, cg18328933, cg15784615 and cg23282949. In this way, information useful to predict the age of the individual is obtained.

Related embodiments of the invention include methods of obtaining information useful to predict an age of an individual by observing methylation patterns one or more specific gene sequences. Illustrative embodiments of this aspect of the invention comprise the steps of obtaining a biological sample derived from an individual comprising genomic DNA from white blood cells or epithelial cells; and then observing a pattern of cytosine methylation occurring on at least one genomic DNA sequence selected from the group consisting of Edaradd (SEQ ID NO: 1), TomL1 (SEQ ID NO: 2), NPTX2 (SEQ ID NO: 3) and ELN (SEQ ID NO: 4). In this way, information useful to predict the age of the individual is obtained. Certain embodiments of the invention observe methylation patterns in multiple gene sequences. Optionally, for example, cytosine methylation is observed in both Edaradd (SEQ ID NO: 1) and TomL1 (SEQ ID NO: 2); and/or both Edaradd (SEQ ID NO: 1) and NPTX2 (SEQ ID NO: 3). In some embodiments of the invention, cytosine methylation is observed in at least two genomic DNA sequences including ELN (SEQ ID NO: 4).

Embodiments of the invention comprise correlating patterns of cytosine methylation with a predicted chronological age of the individual. For example, as disclosed herein, the methylation of certain sites such as the promoters of the EDARADD, TOM1L1, and NPTX2 genes increases with age in a linear manner over a range of five decades. In this context, certain working embodiments use well known mathematical modeling techniques (e.g. regression analyses) to correlate an observed pattern of cytosine methylation a predicted age of the individual. In certain embodiments the methods of the invention can be used to provide valuable information in forensic investigations (e.g. where the identity of the individual from which the DNA is derived is unknown). Such embodiments of the invention can be combined with other forensic analysis procedures, for example by also performing a DNA fingerprinting analysis on the genomic DNA. In other embodiments of the invention, one can compare the predicted age of the individual with the actual chronological age of the individual, for example as part of a diagnostic procedure for an age associated pathology (e.g. one that compares an individual's chronological age with an apparent biological age in view of their DNA methylation patterns). Such methods can be useful in clinical interventions that are predicated on an epigenetic bio-age rather than an actual chronological age.

As discussed in detail below, the methods of the invention can be adapted for use with a variety of art accepted processes. For example, in certain embodiments of the invention, a bisulfite conversion process is performed so that cytosine residues in the genomic DNA are transformed to uracil, while 5-methylcytosine residues in the genomic DNA are not transformed to uracil. Optionally, the genomic DNA is transformed from its natural state via amplification by a polymerase chain reaction process. In certain embodiments of the invention, the genomic DNA is hybridized to a complimentary sequence (e.g. a synthetic polynucleotide sequence) that is coupled to a matrix (e.g. one disposed within a microarray).

Embodiments of the invention also provide articles of manufacture and kits for obtaining information useful to determine the age of an individual. In an illustrative embodiment, the kit includes a plurality of primers or probes specific for at least two genomic DNA sequences in a biological sample, wherein the genomic DNA sequences comprise one or more of the CG loci in the genomic DNA identified in the Table shown in FIG. 4. Such kits of the invention can further include additional reagents, for example a reagent used in a genomic DNA polymerization process, a reagent used in a genomic DNA hybridization process, and/or a reagent used in a genomic DNA bisulfite conversion process. Optionally, the kit comprises a plurality of primer sets for amplifying at least two genomic DNA sequences. In certain embodiments of the invention, the kit comprises primer sets for amplifying at least two genomic DNA sequences in the biological sample selected from the group consisting of Edaradd (SEQ ID NO: 1), TomL1 (SEQ ID NO: 2), NPTX2 (SEQ ID NO: 3) and ELN (SEQ ID NO: 4). In some embodiments of the invention, the kit further comprises a probe or primer used to perform a DNA fingerprinting analysis.

Other objects, features, and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIGS. 4A-4E illustrate 88 loci that are determined to be significantly correlated with age. TargetID represents the exact Illumina probe on the array, Chr: chromosome number, Gene_ID: NCBI Gene database locator, Symbol: gene name, r: correlation coefficient, p-value: significance of correlation, q-value: significance corrected for multiple comparisons.

FIG. 5 illustrates array probes found to be positively correlated with age in blood (see e.g. Rakyan V K, et al. Human aging-associated DNA hypermethylation occurs preferentially at bivalent chromatin domains. *Genome Res* 20: 434-439) and in saliva (present study).

FIG. 6 illustrates disease and molecular function categories significantly enriched in ingenuity analysis.

DETAILED DESCRIPTION OF THE INVENTION

Figure 1:
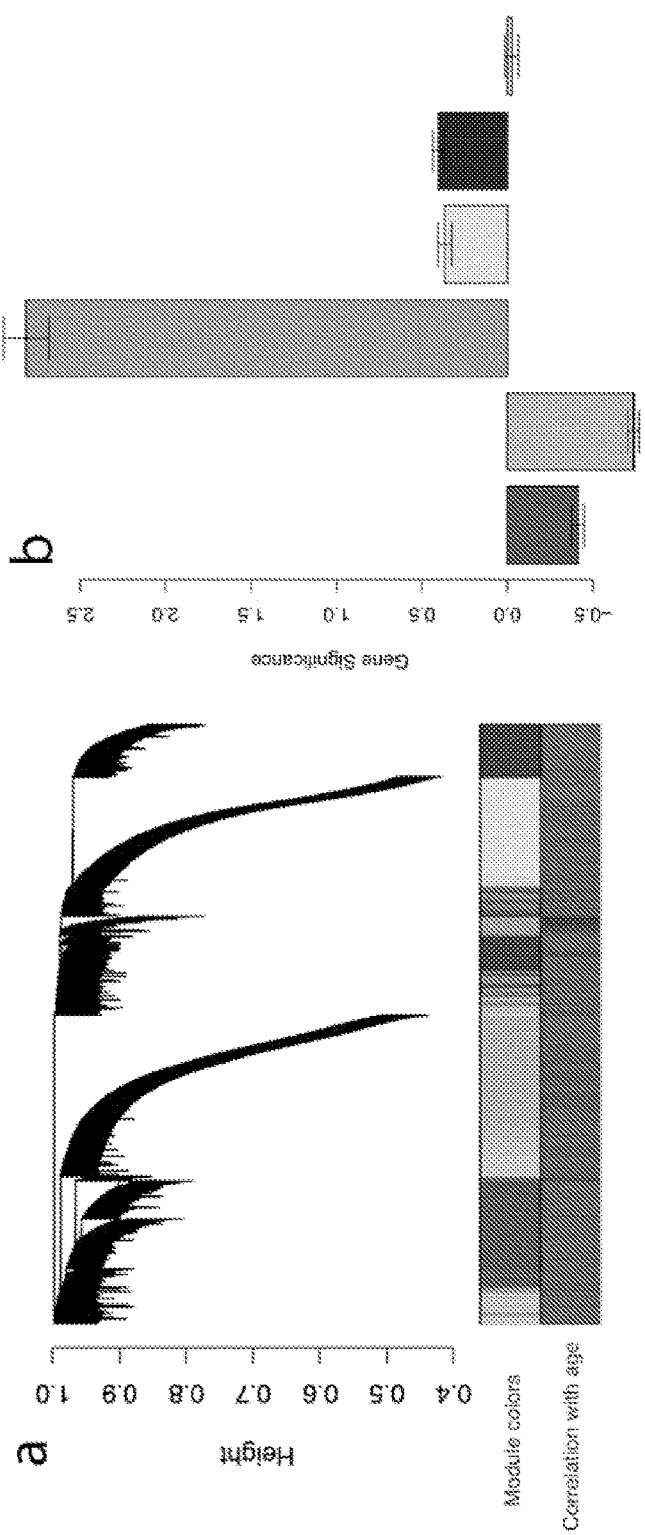
FIG. 1 illustrates the detection of gene co-methylation modules in human saliva in twins. (a) Branches of the hierarchical cluster tree define five co-methylation modules which are assigned a color as can be seen from the first color band underneath the tree. Probes that could not be clustered into one of these modules were coded. Every probe represents a line in the hierarchical cluster tree. Distance between two probes is shown as height on the y-axis. The second band encodes the age relationships of each gene. Genes with positive age correlations are highlighted. (b) Barplots showing age relationships of modules. Specifically, the y-axis shows the mean Student T-statistic testing whether the methylation status of a probe is correlated with age. Note that the module is enriched for probes that have a significant positive correlation with age. A t-statistic value of 2 or higher indicates a significant correlation ($p<0.05$).

Many of the techniques and procedures described or referenced herein are well understood and commonly employed by those skilled in the art. All publications mentioned herein (e.g. U.S. Pat. No. 7,700,324, U.S. Patent Application Nos. 20040132026 and 20060292585, Berdasco et al., Aging Cell (2012) 11, pp 181-186; Bockland et al., et al. (2011) PLoS ONE 6(6): e14821. doi:10.1371/journal.pone.0014821; Koch et al., (2011) AGING, Vol 3, No 10, pp 1,018-1,027) are incorporated herein by reference to disclose and describe aspects, methods and/or materials in connection with the cited publications. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification. In the description of embodiments, reference may be made to the accompanying figures which form a part hereof, and in which is shown by way of illustration a specific embodiment in which the invention may be practiced. It is to be understood that other embodiments may be utilized and structural changes may be made without departing from the scope of the present invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The term "genome" or "genomic" as used herein is all the genetic material in the chromosomes of an organism. DNA derived from the genetic material in the chromosomes of a particular organism is genomic DNA.

The term "epigenetic" as used herein means relating to, being, or involving a modification in gene expression that is independent of DNA sequence. Epigenetic factors include modifications in gene expression that are controlled by changes in DNA methylation and chromatin structure. For example, methylation patterns are known to correlate with gene expression.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). The present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The terms "oligonucleotide" and "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof.

The term "probes" as used herein are oligonucleotides capable of binding in a base-specific manner to a complementary strand of nucleic acid. The term "probe" as used herein refers to a surface-immobilized molecule that can be recognized by a particular target as well as molecules that are not immobilized and are coupled to a detectable label. The term "label" as used herein refers, for example, to colorimetric (e.g. luminescent) labels, light scattering labels or radioactive labels. Fluorescent labels include, inter alia, the commercially available fluorescein phosphoramidites such as Fluoreprime (Pharmacia), Fluoredite (Millipore) and FAM (ABI). See U.S. Pat. No. 6,287,778. See U.S. Pat. No. 6,582,908 for an example of arrays having all possible combinations of probes with 10, 12, and more bases.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa, Nucleic Acids Res. 12:203 (1984), incorporated herein by reference.

The term "hybridization" as used herein refers to the process in which two single-stranded polynucleotides bind non-covalently to form a stable double-stranded polynucleotide; triple-stranded hybridization is also theoretically possible. Factors that can affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004, available at Affymetrix.com.

The term "array" or "microarray" as used herein refers to an intentionally created collection of molecules which can be prepared either synthetically or biosynthetically (e.g. Illumina HumanMethylation27 microarrays). The molecules in the array can be identical or different from each other. The array can assume a variety of formats, for example, libraries of soluble molecules; libraries of compounds tethered to resin beads, silica chips, or other solid supports.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

DESCRIPTION OF ILLUSTRATIVE ASPECTS OF THE INVENTION

From the moment of conception, we begin to age. A decay of cellular structures, gene regulation, and DNA sequence ages cells and organisms. For example, DNA methylation patterns change with increasing age and contribute to age related disease. Methylation in promoter regions is generally accompanied by gene silencing and loss of methylation or loss of the proteins that bind to the methylated CpG can lead to diseases in humans, for example, Immunodeficiency Craniofacial Syndrome and Rett Syndrome, Bestor (2000) Hum. Mol. Genet. 9:2395-2402. DNA methylation may be gene-specific and occurs genome-wide.

A variety of methods for detecting methylation status or patterns have been described in, for example U.S. Pat. Nos. 6,214,556, 5,786,146, 6,017,704, 6,265,171, 6,200,756, 6,251,594, 5,912,147, 6,331,393, 6,605,432, and 6,300,071 and US Patent Application publication Nos. 20030148327, 20030148326, 20030143606, 20030082609 and 20050009059, each of which are incorporated herein by reference. Other array based methods of methylation analysis are disclosed in U.S. patent application Ser. No. 11/058,566. For a review of some methylation detection methods, see, Oakeley, E. J., Pharmacology & Therapeutics 84:389-400 (1999). Available methods include, but are not limited to: reverse-phase HPLC, thin-layer chromatography, SssI methyltransferases with incorporation of labeled methyl groups, the chloracetaldehyde reaction, differentially sensitive restriction enzymes, hydrazine or permanganate treatment (m5C is cleaved by permanganate treatment but not by hydrazine treatment), sodium bisulfite, combined bisulphate-restriction analysis, and methylation sensitive single nucleotide primer extension.

As disclosed herein, a number of locations have been identified in the human genome for which the percentage of DNA methylation is linearly correlated with age. By measuring this DNA methylation at the disclosed locations, for example, at just a few of the 3 billion letters in a person's genome, the present invention is able to make accurate estimates of a person's chronological age. While previous studies have shown that DNA methylation in certain parts of the genome changes with age, the experiments disclosed herein are the first to identify loci where methylation is continuously correlated with age, over a range of at least 5 decades. The strength of this finding allows the present invention to accurately predict an individual's age. In certain embodiments of the invention, the link between age and this chemical change in the DNA is so strong that it is possible to estimate how old someone is by examining, for example, just two spots in the genome of the individual. Aspects of the invention have been published in a peer reviewed technical journal (see Bockland et al., et al. (2011) PLoS ONE 6(6): e14821. doi:10.1371/journal.pone.0014821). In addition, certain aspects of this research have been confirmed by other studies (see, e.g. Koch et al., (2011) AGING, Vol 3, No 10, pp 1,018-1,027)

As described in detail in the Example below, specific age related methylation markers have been identified and validated using further assays and additional samples. As discussed below, illustrative age prediction analyses models were also designed and tested, for example using a leave-one-out analysis, where one subject from the model is systematically removed and the model is used to predict the subject's age. As the real age of this subject is already known, such methods provided ways to validate various model designs. Such age predictive models can be applied in a variety of contexts. For instance, the ability to predict an individual's age (e.g. to an average accuracy of 3 to 5 years) can be used by forensic scientists to estimate a suspect's age based on a biological sample alone. In embodiments of the invention designed for forensic use, a practitioner could, for example, submit a biological sample to a lab. In the lab, DNA prepared from the sample could then be analyzed anso that the percentage of methylation at one or more of the loci identified herein is determined. These results could be input in a regression model such as those disclosed herein, in order to predict the age of the suspect.

Age prediction methodologies are also relevant to healthcare applications. For example, significant DNA methylation differences are know to be associated with specific age-related disorders, for example in comparisons between the brains of people diagnosed with late-onset Alzheimer's disease and brains from controls. In this context, the identification of specific loci highly correlated with age can be used to enhance the understanding of aging in health and disease. In certain embodiments of the invention, age prediction methodologies can be used as part of clinical interventions tailored for patients based on their "bio-age"—a result of the interaction of genes, environment, and time—rather than their chronological age. For example, if a person's predicted age is higher than their real age, specific interventions could be designed to return the genome to a "younger" state. Age prediction methodologies can also pave the way for interventions based on specific epigenetic marks associated with disease, as occurs in certain cancer treatments.

The invention disclosed herein has a number of embodiments. As shown by the experiments disclosed herein, 88 sites have been identified in or near 80 genes for which the degree of cytosine methylation significantly correlates with age, for example, in biological samples obtained from the saliva of 34 male identical twin pairs between 21 and 55 years of age. There are more than 28 million CpG loci in the human genome. Consequently, certain loci are given unique identifiers such as those found in the Illumina CpG loci database (see, e.g. Technical Note: Epigenetics, *CpG Loci Identification* ILLUMINA Inc. 2010). These CG locus designation identifiers are used herein. In this context, one embodiment of the invention is a method of obtaining information useful to determine an age of an individual by observing the methylation status of one or more specific GC loci that are identified in FIG. 4. A related embodiment of the invention is a method of obtaining information useful to determine an age of an individual by observing the methylation status of one or more cytosines in genomic DNA that is within 1 kilobase on either side of the specific GC loci that are identified in FIG. 4 (see, e.g., Table 1 below).

Embodiments of the invention comprise the steps of obtaining genomic DNA from leukocytes or epithelial cells derived from the individual and then observing cytosine methylation of one or more (and typically two, three, four or more) CG loci in the genomic DNA. Leukocytes and/or epithelial cells can be derived from a variety of biological samples (e.g. saliva, blood, semen, skin and the like). Such samples can, for example, be treated with a reagent effective for opening the cells, fluids, tissues, cell membranes of the sample, and for exposing the nucleic acid(s). Methods for purifying or partially purifying nucleic acid from a sample are well known in the art (e.g., Sambrook et al., Molecular Cloning: a Laboratory Manual. Cold Spring Harbor Press, 1989, herein incorporated by reference).

In illustrative embodiments of the invention, methylation is observed in one or more CG loci selected from the group consisting of CG locus designation: cg27553955, cg12799895, cg21296230, cg04084157, cg25148589, cg17861230, cg03734874, cg18236477, cg27320127, cg07621046, cg14456683, cg21801378, cg00107187, cg05508084, cg07533148, cg03975694, cg19945840, cg00399483, cg06291867, cg24826867, cg06092815, cg19885761, cg24199834, cg04528819, cg13434842, cg02008154, cg25044651, cg02994956, cg20366906, cg27389185, cg14826456, cg12111714, cg12457773, cg11981599, cg00059225, cg06572160, cg08668790, cg12782180, cg20134215, cg13921352, cg13614181, cg23563234, cg00201234, cg21992250, cg00911351, cg19594666, cg15425280, cg06156376, cg19831077, cg27409364, cg15747595, cg02154186, cg20616414, cg10235817, cg16232126, cg24646414, cg17241310, cg10031651, cg23290344, cg06908778, cg02844545, cg14614211, cg25511429, cg15201635, cg19246110, cg06760035, cg13603171, cg13282837, cg20792062, cg02228185, cg13547237, cg09809672, cg01293143, cg05822532, cg07408456, cg08468689, cg27210390, cg01820374, cg17589341, cg19761273, cg03440846, cg08909157, cg11136562, cg16464322, cg08872742, cg18328933, cg15784615 and cg23282949. In this way, information useful to determine the age of the individual is obtained.

As a confirmation of the significance of the CpG loci data obtained using Illumina HumanMethylation27 microarrays, certain sites were validated, for example those in the promoters of the EDARADD, TOM1L1, and NPTX2 genes. The results were then replicated in a general population sample of 31 males and 29 females between 18 and 70 years of age. These validation studies confirm, for example, that the methylation of sites including those in the promoters of the EDARADD, TOM1L1, and NPTX2 genes, is linear with age over a range of at least five decades. Table 1 below shows the surrounding sequences and the exact location of certain CpGs of interest in the Edaradd, Tom1L1, NPXT2 and ELN sequences. Different font emphasis is used to show the location of the PCR primers, of the sequencing primers (for two genes, the third gene was measured using different methods as discussed in the text) as well as the CpGs found to be correlated with age. Font emphasis is also used for other CpGs that can be read in the same experiment and be correlated with age. As shown in Table 1, NPTX2 has more than one CpG that are underlined (CpG 1, 2, 4 and 6 starting from the sequencing primer). These have been shown to be correlated with age as well. The methylation status of one of these is highly predictive of the methylation of the others nearby, so any one of them can be used in the predictive models disclosed herein. Those of skill in this art understand that the CpGs in the vicinity of the relevant ones can further be examined in embodiments of the invention (e.g. because methylation status is sometimes clustered on those CpGs for hundreds or thousands of basepairs away).

Embodiments of the invention include methods of obtaining information useful to determine an age of an individual by observing methylation patterns one or more specific gene sequences. Such embodiments comprise the steps of obtaining a biological sample derived from an individual comprising genomic DNA from white blood cells or epithelial cells; and then observing a pattern of cytosine methylation of at least one genomic DNA sequence selected from the group consisting of Edaradd (SEQ ID NO: 1), TomL1 (SEQ ID NO: 2), NPTX2 (SEQ ID NO: 3) and ELN (SEQ ID NO: 4). In this way, information useful to determine the age of the individual is obtained. Optionally, for example, cytosine methylation is observed in both Edaradd (SEQ ID NO: 1) and TomL1 (SEQ ID NO: 2); and/or both Edaradd (SEQ ID NO: 1) and NPTX2 (SEQ ID NO: 3). In some embodiments of the invention, cytosine methylation is observed in at least two genomic DNA sequences including ELN (SEQ ID NO: 4). Typically in these methods, cytosine methylation is observed one or more cytosine residues having a CG locus designation: cg09809672, cg27210390, cg12799895 or cg05822532. Certain embodiments of the invention observe methylation in other gene sequences of the genes identified in FIGS. 4 and 5, such as TRIM58 as well as GRIA2 (see also Koch et al., (2011) AGING, Vol 3, No 10, pp 1,018-1,027).

Related embodiments of the invention include methods of obtaining information useful to determine an age of an individual by obtaining a biological sample derived from an individual comprising genomic DNA from white blood cells or epithelial cells; and then observing a degree of cytosine methylation of at least one genomic DNA sequence of a gene selected from the group consisting of KCNG3, NPTX2, GREM1, VGF, GRIA2, PDE4C, FLJ42486, ATP8A2, KCNK12, C10orf82, ZIC1, BRUNOL6, ZNF667, TRIM58, ZNF540, B3GALT6, DCC, HTR7, IRF8, SKIP, CPLX2, POU4F2, KLF14, GATA4, TBX20, FLJ90650, NEFH, PCDH8, ADRB1, VMP, GLRA1, KCNG3, ZNF154, LEP, MCHR2, FAM19A4, RGC32, PCDHGB7, FBLN2, SLC15A3, PCDHGB4, SHOX2, LOC349136, KCNC1, TSPYL5, PNMA2, WNK2, ADRA2C, SLC5A7, BARHL2, LRRC2, NEF3, SPAG6, GCM2, IRXL1, NRN1, SMPD3, ZNF671, HOXB4, MOXD1, TCL1A, KCNA5, ASPA, Bles03, EDARADD, TCEA2, ELN, PGLYRP2, LGP1, TOM1L1, LAG3, SLC14A1, CSNK1D, ACSS2, C9orf66, CENTD3, HNRPL, CDH5, ABHD14A, LTBR, and RENBP. In embodiments of the invention, these sequences can include either translated or untranslated 5' regulatory regions; and optionally are within 1 kilobase (5' or 3') of the specific GC loci that are identified in FIG. 4. These methods can further comprise correlating the degree/amount of cytosine methylation observed in the sequence with a predicted age of the individual, so that information useful to determine the age of the individual is obtained.

Embodiments of the invention include methods where observations of cytosine methylation in genomic DNA from a biological sample are used to predict the chronological age of the individual from which a sample is derived. In certain embodiments the methods of the invention can be used to provide valuable information in forensic investigations (e.g. where the identity of the individual from which the DNA is derived is unknown). Such embodiments of the invention can be combined with other forensic analysis procedures, for example by also performing a DNA fingerprinting analysis on the genomic DNA. DNA fingerprinting (also known as DNA profiling) using short tandem repeats (STRs) is one method for human identification in forensic sciences, finding applications in different circumstances such as determination of perpetrators of violent crime, resolving paternity, and identifying remains of missing persons or victims of mass disaster. The FBI and the forensic science community typically use 13 separate STR loci (the core CODIS loci) in routine forensic analysis. (CODIS refers to the Combined DNA Index System that was established by the FBI in 1998). Illustrative DNA fingerprinting methodologies are disclosed, for example, in U.S. Pat. Nos. 7,501,253, 7,238,486, 6,929,914, 6,251,592, and 5,576,180).

In addition, a measurement of relevant methylation patterns in genomic DNA from white blood cells or skin cells also provides a tool in routine medical screening to predict the risk of age-related diseases as well as to tailor interventions based on the epigenetic bio-age instead of the chronological age. In some embodiments of the invention, one can compare the predicted age of the individual with the actual chronological age of the individual, for example as part of a diagnostic procedure for an age associated pathology (e.g. one that compares an individual's chronological age with an apparent biological age in view of their DNA methylation patterns). Such methods can be useful in clinical interventions that are predicated on an epigenetic bio-age rather than an actual chronological age. In one embodiment, a biological sample can be collected in a routine health check and sent to the lab for methylation pattern analysis (e.g. as described above). If the predicted age of the patient is higher than the real age, the patient can be at an increased risk of age-related diseases, and dietary intervention, or specific drugs, could be prescribed to reduce this "genetic age".

As noted above, embodiments of the invention include methods of obtaining information useful to determine a level of risk of an age-related disease in an individual (e.g. Alzheimer's disease or Parkinson's disease). Typically, these methods comprise the steps of obtaining a biological sample derived from an individual comprising genomic DNA from white blood cells or epithelial cells and then observing a degree of cytosine methylation of at least one genomic DNA sequence of a gene selected from the group consisting of KCNG3, NPTX2, GREM1, VGF, GRIA2, PDE4C, FLJ42486, ATP8A2, KCNK12, C10orf82, ZIC1, BRUNOL6, ZNF667, TRIM58, ZNF540, B3GALT6, DCC, HTR7, IRF8, SKIP, CPLX2, POU4F2, KLF14, GATA4, TBX20, FLJ90650, NEFH, PCDH8, ADRB1, VMP, GLRA1, KCNG3, ZNF154, LEP, MCHR2, FAM19A4, RGC32, PCDHGB7, FBLN2, SLC15A3, PCDHGB4, SHOX2, LOC349136, KCNC1, TSPYL5, PNMA2, WNK2, ADRA2C, SLC5A7, BARHL2, LRRC2, NEF3, SPAG6, GCM2, IRXL1, NRN1, SMPD3, ZNF671, HOXB4, MOXD1, TCL1A, KCNA5, ASPA, Bles03, EDARADD, TCEA2, ELN, PGLYRP2, LGP1, TOM1L1, LAG3, SLC14A1, CSNK1D, ACSS2, C9orf66, CENTD3, HNRPL, CDH5, ABHD14A, LTBR, and RENBP. In embodiments of the invention, these sequences can include either translated or untranslated 5' regulatory regions; and optionally are within 1 kilobase (5' or 3') of the specific GC loci that are identified in FIG. 4. Embodiments of these methods further comprise calculating a theoretical bio-age of the individual based on the degree/amount of cytosine methylation observed in the sequence and then comparing the theoretical bio-age of the individual to an actual chronological age of the individual. In this way, information useful to determine a level of risk of an age-related disease in the individual is obtained. Optionally for example, the theoretical bio-age of the individual is compared to an actual chronological age to determine if the theoretical bio-age is greater than the actual chronological age; and the method further include providing an individualized treatment to the individual to bring the theoretical bio-age closer to the actual chronological age of the individual.

As noted above, embodiments of the invention can comprise correlating patterns of cytosine methylation with a predicted chronological age of the individual. For example, as disclosed herein, the methylation of certain sites such as the promoters of the EDARADD, TOM1L1, and NPTX2 genes increases with age in a linear manner over a range of five decades. In this context, illustrative working embodiments of the invention use a regression analysis to correlate an observed pattern of cytosine methylation the predicted age of the individual. Using just two cytosines from the EDARADD, TOM1L1, and NPTX2 loci, a regression model was designed that explains 73% of the variance in age, and is able to predict the age of an individual with an average accuracy of 5.2 years.

Using conventional regression model/analysis tools and methodologies known in the art, a number of age prediction models can be designed for use with specific genomic DNA samples and/or specific analysis techniques and/or specific individual populations (see, e.g., statistical package R version 2.11.1 in citation as discussed in R Development Core Team (2005) R: A language and environment for statistical computing. R Foundation for Statistical Computing, Vienna, Austria. ISBN 3-900051-07-0, URL www.R-project.org). In addition to the illustrative models disclosed herein, other models can, for example, customize the coefficient values (weights) for different tissues and/or cell lineages. In addition to tissue type, such coefficients can be weighted in data sets from different populations. For example, if a model is applied to pediatric patients only, then one set of coefficients can be used. Alternatively, if a model is applied exclusively to older people (say >50 years), another set of coefficients can be used. Alternatively, coefficients can be fixed, when for example, a model is broadly applied to people of ages from 10 to 100 etc. Coefficient values in various models can also reflect the specific assay that is used to measure the methylation levels (e.g. as the variance of the methylation levels of individual probes may affect the coefficient). For example, for beta values measured on the Illumina methylation microarray platforms there can be one set of coefficients, while for other methylation measures (e.g. using sequencing technology) there can be another set of coefficients etc. In practicing certain embodiments of the invention, one can collect a reference data set (e.g. of 100 individuals of varying ages) using specific technology platform(s) and tissue(s) and then design a specific multivariate linear model is fit to this reference data set to estimate the coefficients (e.g. using least squares regression). The resultant multivariate models can then be used for predicting ages on test patients. In this way, different mathematical models can be adapted for analyzing methylation patterns in a wide variety of contexts.

As discussed in detail below, in addition to using art accepted modeling techniques (e.g. regression analyses), embodiments of the invention can include a variety of art accepted technical processes. For example, in certain embodiments of the invention, a bisulfite conversion process is performed so that cytosine residues in the genomic DNA are transformed to uracil, while 5-methylcytosine residues in the genomic DNA are not transformed to uracil. Kits for DNA bisulfite modification are commercially available from, for example, Human Genetic Signatures' Methyleasy and Chemicon's CpGenome Modification Kit. See also, WO04096825A1, which describes bisulfite modification methods and Olek et al. Nuc. Acids Res. 24:5064-6 (1994), which discloses methods of performing bisulfite treatment and subsequent amplification. Bisulfite treatment allows the methylation status of cytosines to be detected by a variety of methods. For example, any method that may be used to detect a SNP may be used, for examples, see Syvanen, Nature Rev. Gen. 2:930-942 (2001). Methods such as single base extension (SBE) may be used or hybridization of sequence specific probes similar to allele specific hybridization methods. In another aspect the Molecular Inversion Probe (MIP) assay may be used.

In certain embodiment of the invention, the genomic DNA is hybridized to a complimentary sequence (e.g. a synthetic polynucleotide sequence) that is coupled to a matrix (e.g. one disposed within a microarray). Optionally, the genomic DNA is transformed from its natural state via amplification by a polymerase chain reaction process. For example, prior to or concurrent with hybridization to an array, the sample may be amplified by a variety of mechanisms, some of which may employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159, 4,965,188, and 5,333,675. The sample may be amplified on the array. See, for example, U.S. Pat. No. 6,300,070 which is incorporated herein by reference.

Another embodiment of the invention is a kit for obtaining information useful to determine the age of an individual, the kit comprising a plurality of primers or probes specific for at least one genomic DNA sequence in a biological sample, wherein the genomic DNA sequences comprises a CG loci identified in FIG. 4. Such kits of the invention can further include a reagent used in a genomic DNA polymerization process, a genomic DNA hybridization process, and/or a genomic DNA bisulfite conversion process. In some embodiments of the invention, the kit comprises a methylation microarray (see, e.g. U.S. Patent Application Publication no. 20060292585, the contents of which are incorporated by reference). Optionally, the kit comprises a plurality of primer sets for amplifying at least two genomic DNA sequences. In certain embodiments of the invention, the kit comprises primer sets for amplifying at least two genomic DNA sequences in the biological sample selected from the group consisting of Edaradd (SEQ ID NO: 1), TomL1 (SEQ ID NO: 2), NPTX2 (SEQ ID NO: 3) and ELN (SEQ ID NO: 4). In some embodiments of the invention, the kit further comprises a probe or primer used to perform a DNA fingerprinting analysis.

EXAMPLES

The present invention is described in detail in the following example, but is not limited by any aspect of this example.

Example 1: Typical Methods and Materials Useful for Practicing Embodiments of the Invention Genomic DNA Collection Protocols Saliva was collected using Oragene DNA collection kits (Genotek). The majority (up to 74%) of the DNA in saliva collected with this method comes from white blood cells, with the remainder being buccal epithelial cells (see, e.g. Thiede C, et al. (2000) Buccal swabs but not mouthwash samples can be used to obtain pretransplant DNA fingerprints from recipients of allogeneic bone marrow transplants. *Bone Marrow Transplant* 25: 575-577). Genomic DNA was prepared according to the manufacturer's protocol. Zygosity was determined using 9 microsatellite markers. Microarray hybridization was performed by the Southern California Genotyping Consortium at UCLA. 500 ng of genomic DNA was bisulfite converted using the EZ-methylation kit (Zymo Research), and processed according to the Illumina Infinium whole genome genotyping protocol. Labelled samples were hybridized to Illumina HumanMethylation27 arrays, scanned (iScan reader, Illumina), and beta (methylation) values extracted using GenomeStudio software.

Analysis: A signed weighted correlation network was constructed as described (see, e.g. Zhang B, et al. (2005) A general framework for weighted gene co-expression network analysis. *Stat Appl Genet Mol Biol* 4: Article 17; Langfelder P, et al. (2008) WGCNA: an R package for weighted correlation network analysis. *BMC Bioinformatics* 9: 559). Module definition was based on the gene methylation status in saliva and ignored age. As module representative, we used the module eigenlocus (ME) which is defined as the first principal component of the module methylation profiles and can be considered a weighted average. To incorporate age into the network analysis, the Student t-test statistic for correlating age with methylation status was used. Lasso penalized regression was performed using the 'penalized' package of R (see, e.g. Wu T T, et al. (2009) Genome-wide association analysis by lasso penalized logistic regression. *Bioinformatics* 25: 714-721). All statistical analyses and data processing were performed using the statistical package R version 2.11.1 (see, e.g. R Development Core Team (2005) R: A language and environment for statistical computing. R Foundation for Statistical Computing, Vienna, Austria. ISBN 3-900051-07-0, URL http://www.R-project.org). PCR primers and conditions for amplification, massarray and pyrosequencing analysis are described below.

PCR Protocol and Primers 500 ng of genomic DNA was bisulfite converted using the EZ-methylation kit (Zymo Research), and 10 ng was used for each reaction. Edaradd was amplified using Bio-x-act Long (Bioline) with 20 seconds annealing at 57° C., and 30 seconds extension at 68° C., for 40 cycles. Tom1L1 and NPTX2 were amplified using Sahara Mix (Bioline) with 20 seconds annealing at 58° C. (Tom1L1) or at 55° C. (NPTX2), and 25 seconds extension at 72, for 40 cycles. Primer sequences for the amplicons are listed below. The appropriate sequence tags were added to the Edaradd PCR primers according to the instructions provided by Sequenom.

Edaradd methylation was assayed using MassArray (Sequenom) by the Genomics Core of the Albert Einstein College of Medicine, and the percent methylation at each CpG site extracted with EpiTyper software (Sequenom). Tom1L1 and NPTX2 methylation was assayed using Pyrosequencing by the UCLA Genotyping and Sequencing Core.

```
Edaradd:
                                   (SEQ ID NO: 5)
F: GGTAGATTAAGAGGAAGTTTATTTTTTAT (SEQ ID NO: 6)
R: AATACCTCTCCCCATCTATTTAATC Tom1L1:
                                   (SEQ ID NO: 7)
F: TTAATTTATTGTAGAATTTT (SEQ ID NO: 8)
R: AAACCTCCTCTTCTAATCTATAAAAC Sequencing primer:
                                   (SEQ ID NO: 9)
ATAAAATATTTAAACCTCCA

NP TX2:
                                   (SEQ ID NO: 10)
F: TAGTTTAAGAAAGGG (SEQ ID NO: 11)
R: AACTATCCTAAACCCCAAC

Sequencing primer:
                                   (SEQ ID NO: 12)
ACAAAAAACTTCTACCC
```

Microarray Analysis

Monozygotic (MZ) twins form an attractive model to study methylation changes with age. At the time of separation both embryos have nearly identical methylation patterns. While certain methylation changes are genetically controlled, environmental exposure and stochastic processes can also lead to a change in methylation patterns. In this context, identical twins can be considered replicates of the same developmental and aging experiment.

In this study we quantified the methylation status of 27,578 CpG loci covering more than 14,000 genes at single-nucleotide resolution in saliva samples of 34 pairs of identical twins, between 21 and 55 years of age, using Illumina HumanMethylation27 microarrays. Monozygosity was verified for all pairs by analysis of nine short tandem repeat probes. For each CpG site on the microarray, we calculated the beta value, which expresses the fraction of methylated cytosines in that location. A site that is completely methylated on both alleles in all cells has a beta value equal to 1; a completely unmethylated site equals 0. All subsequent analyses were performed on this beta value. For computational reasons, the data was filtered by requiring a mean methylation value between 0.05 and 0.95, and variance greater than 0. The resulting restricted dataset contained 16,155 probes, and all further analyses were performed on this filtered dataset. Batch effect were removed using the Combat algorithm (see, e.g. Johnson W E, et al. (2007) Adjusting batch effects in microarray expression data using empirical Bayes methods. *Biostatistics* 8: 118-127), and one outlier sample was removed.

Figure 7:
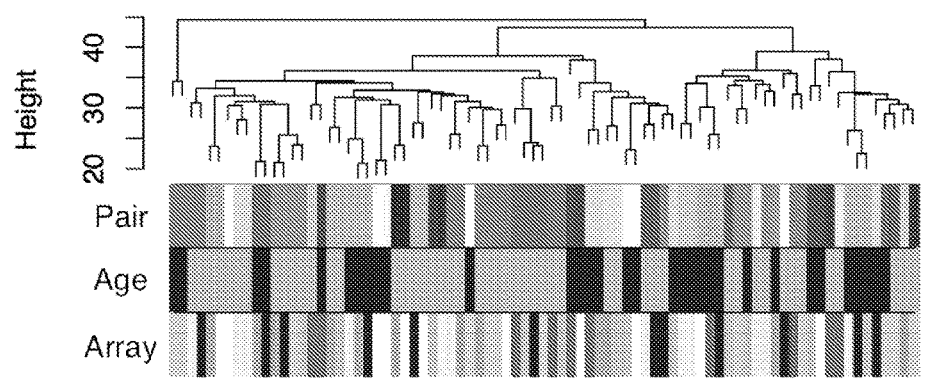
FIG. 7 illustrates unsupervised hierarchical clustering of all samples. The y-axis shows distance between samples. Each twin pair is color coded. Row "Pair" shows that the majority of twin pairs cluster together. Samples were divided in the oldest and youngest half and coded dark and light blue. Row "Age" shows that samples of similar age group did not cluster together. The different arrays were each color coded as well, and row "Array" shows that samples hybridized together do not cluster together, suggesting that variations in hybridization do contribute to the data analysis.

We first determined whether methylation differences measured using these arrays reflected actual differences between individuals by calculating the correlation coefficient between replicate arrays for 10 samples. The median correlation between replicate arrays was 0.995 (range 0.990-0.996), compared to 0.987 (range 0.957-0.994) between unrelated samples. This difference was highly significant (Wilcoxon test, $p=1.4\times10^{-7}$). In unsupervised hierarchical clustering, the majority of twin pairs clustered together (FIG. 7) and twin samples correlated with $r=0.992$ (range 0.983-0.997), which is significantly different from the correlation between unrelated samples (Wilcoxon test, $p=1.93\times10^{-11}$).

A previous study showed increasing global epigenetic differences with age in a sample of identical twins, suggesting increased epigenetic drift with age (see, e.g. Fraga M F, et al. (2005) Epigenetic differences arise during the lifetime of monozygotic twins. *Proc Natl Acad Sci USA* 102: 10604-10609). We were unable to replicate these genome-wide methylation changes when the intra-pair correlation coefficients, the intra-pair Euclidian distance, or the intra-pair Manhattan distance was correlated with age (p>0.1). We did, however, identify a subset of loci to be highly correlated with age.

A recurrent problem with data analysis on a whole genome scale is correcting for multiple comparisons. The stringency level of the chosen correction method strongly affects the odds of identifying significant findings. We previously described weighted correlation network analysis (WGCNA) as a data reduction scheme (see, e.g. Horvath S, et al. (2008) Geometric interpretation of gene coexpression network analysis. *PLoS Comput Biol* 4: e1000117; Zhang B, et al. (2005) A general framework for weighted gene co-expression network analysis. *Stat Appl Genet Mol Biol* 4: Article 17). Here we used WGCNA to identify modules of loci with highly similar methylation values. First, we averaged all methylation values for each twin pair, and treated each pair's data as an individual sample. Since both twins are genetically identical and of the same age, averaging the data reduces possible environmental effects on DNA methylation. After hierarchical clustering of the data set, branches of the cluster dendrogram defined five modules ranging in size from 199 to 842 loci, of which the methylation values were highly correlated across the samples (FIG. 1A). We color-coded the modules, calculated a weighted average, representative locus (eigenlocus) for each module (see methods) and correlated this with age. The correlation between age and the representative of the green module was highly significant ($r=0.62$, $p=7.2\times10^{-5}$, FIG. 1B), even after using the most stringent multiple comparison correction (Bonferroni), since only 5 comparisons—corresponding to 5 modules—were carried out. Module membership of all probes can be found in FIG. 7.

Identification of 88 Novel Loci Correlated with Age

To identify novel loci for which the methylation values correlate positively or negatively with age, we calculated q-values to correct for multiple comparisons (see, e.g. Storey J D, et al. (2003) Statistical significance for genomewide studies. *Proc Natl Acad Sci USA* 100: 9440-9445). We selected probes with q-values smaller than 0.05, corresponding to absolute correlation values greater than 0.57. A total of 88 probes correlated with age (FIG. 4), corresponding to 80 genes spread over several of the modules. Of these, 19 probes were negatively correlated, and 69 were positively correlated with age, of which 57 belonged to the green module. A recently published study used a very similar study design and identical microarrays to identify 131 CpG sites correlated with age in blood samples of identical twins ranging from 49 to 75 years of age (see, e.g. Rakyan V K, et al. (2010) Human aging-associated DNA hypermethylation occurs preferentially at bivalent chromatin domains. *Genome Res* 20: 434-439). Of these 131 sites, 10 were found to be positively correlated with age in our study as well (FIG. 5).

Of the 88 probes that were significantly correlated with age in our study, only one was near a gene encoding a microRNA (HSA-MIR-10A, in the HOXB4 gene), which was not different from the density on the array. 73 of 88 (83%) significant probes were within CpG-islands, thus this probe set was enriched in CpG islands relative to the typical array probe (73% in CpG islands, p=0.031, Fisher's exact test for count data). CpG sites that were significantly correlated with age were a median 238 base-pairs upstream of the transcription start site.

Ingenuity analysis showed the 80 age-related genes were highly enriched for genes involved in cardiovascular disease ($p=1.59\times10^{-6}$), neurological disease ($p=1.47\times10^{-4}$), and genetic disease ($p=1.59\times10^{-6}$)—a category consisting almost entirely of the cardiac and neurological genes as well. The most enriched cellular function was molecular transport ($p=2.4\times10^{-3}$). The full gene ontology analysis can be found in FIG. 6.

Validation of Correlated Probes in Additional Samples

Figure 2:
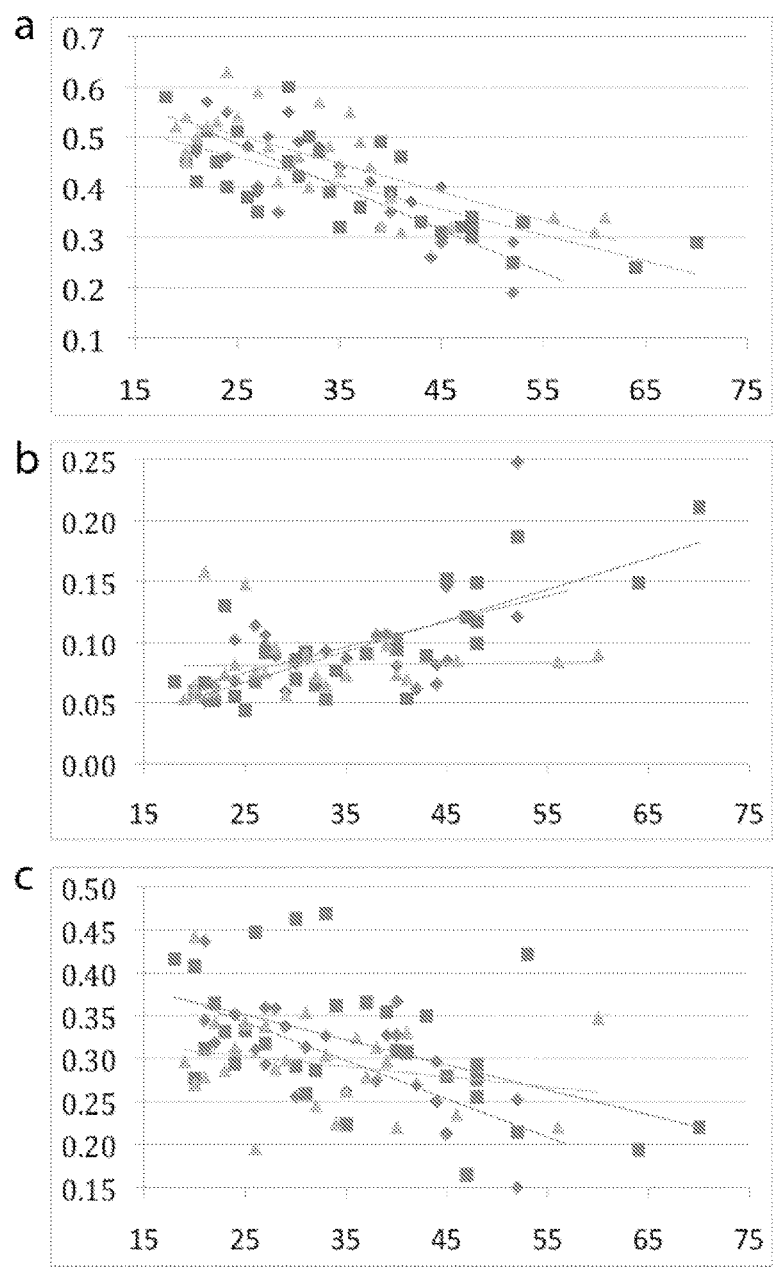
FIG. 2 illustrates percentage methylation versus age for three markers validated in three sample sets. Original twin samples are blue, male control samples are red, female control samples green. Linear trendlines are shown in the colors of the individual sample sets a) Edaradd $r=-0.81$ (twins), $r=-0.73$ (male controls), $r=-0.75$ (female controls) b) NPTX2 $r=0.52$ (twins), $r=0.79$ (male controls), $r=0.03$ (female controls) c) Tom1L1 $r=-0.70$ (twins), $r=-0.49$ (male controls), $r=-0.24$ (female controls).

Three probes for which the methylation status was highly correlated with age, and which had the widest distribution of values, were chosen for further validation. Saliva samples from 22 twins from the array study, 31 unrelated male, and 29 unrelated female samples (age range=18-70 years-old) were bisulfite converted and PCR amplified. The fraction of methylated cytosines at the exact CpG sites assayed on the Illumina arrays were quantified by MassArray (Sequenom) for the Edaradd gene and by pyrosequencing for NPTX2 and Tom1L1. For NPTX2, the pyrosequencing method provided methylation data for five additional CpG sites in the promoter. The results of the validation experiments correlated very strongly with the array data for all three genes (Edaradd $r=0.96$, NPTX2 $r=0.92$, Tom1L1 $r=0.90$, n=23), providing a technical replication of the array data in the twin sample. The correlation between the degree of methylation and age of all three genes was preserved in the subset of twins and was also found in the independent male sample, providing a biological replication. In females, Edaradd and Tom1L1 were significantly correlated with age, but NPTX2 was not. The correlation results are shown in FIG. 2. A multivariate linear regression model using Edaradd, Edaradd squared and NPTX2 showed that these two markers explain 76% (or $R^2=0.76$) of the variance in age of males and 70% in females. When considering males and females together the model explained 73% of the variance in age.

A Leave-One-Out Analysis Forms an Accurate Epigenetic Predictor of Age

Figure 3:
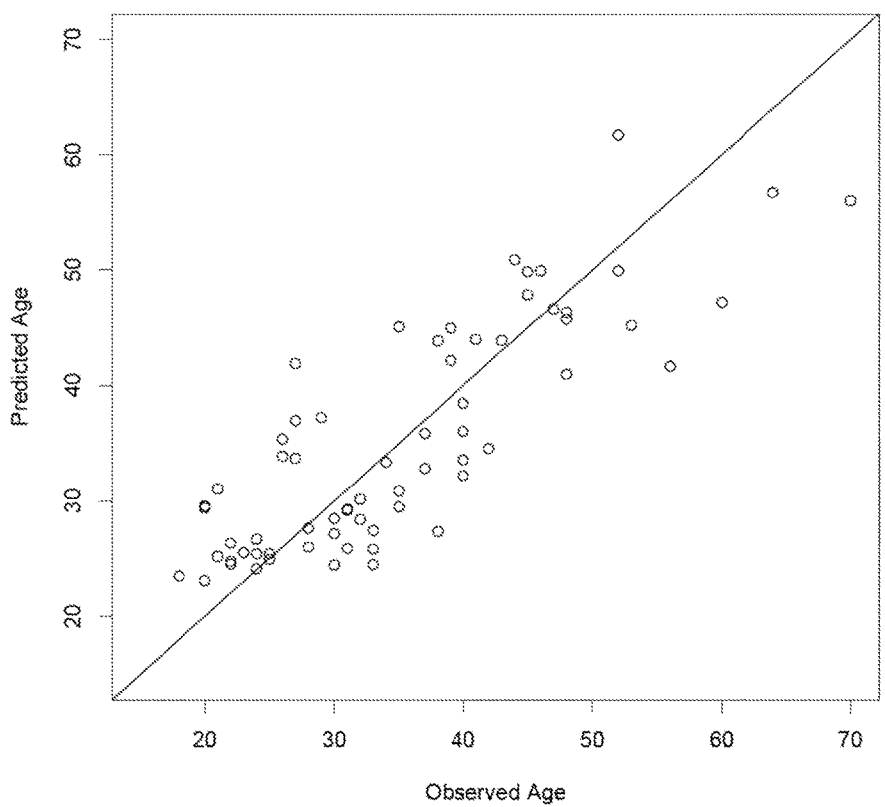
FIG. 3 illustrates predicted versus observed age of all subjects using a leave-one-out model. A multivariate regression model was fit on all but one sample and its predicted age (y-axis) was related to the truly observed age of the left out sample (x-axis). The predicted values are highly correlated with the observed ages ($r=0.83$, $p=2.2\times10^{-16}$, $n=66$), and the average absolute difference between the predicted and the observed age is 5.2 years.
Figure 8:
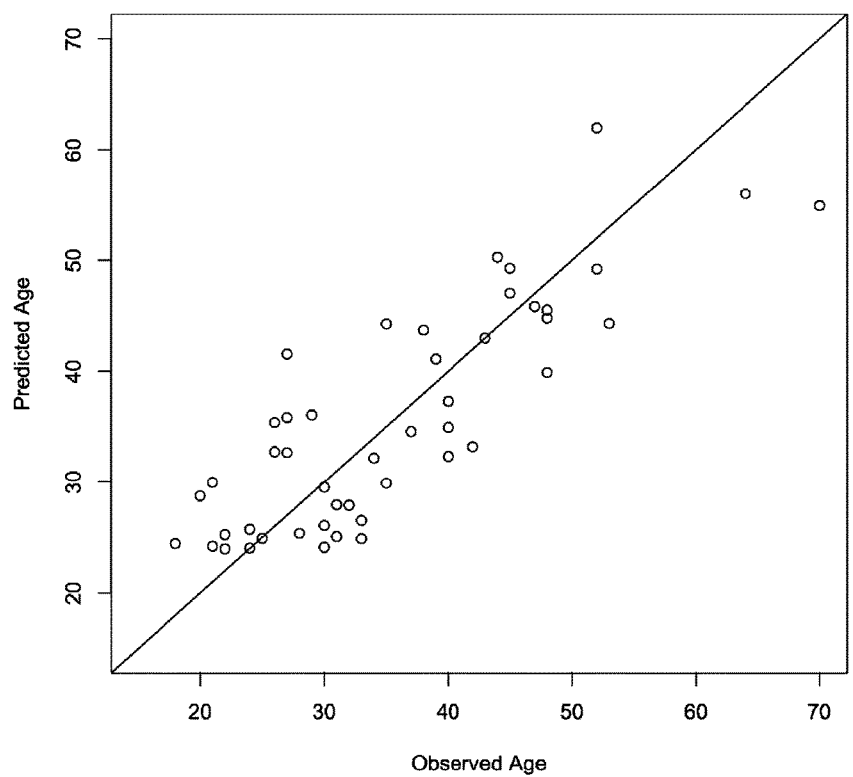
FIG. 8 illustrates predicted versus observed age of all male subjects using a leave-one-out model. A multivariate regression model was fit on all but one sample and its predicted age (y-axis) was related to the truly observed age of the left out sample (x-axis). The predicted values are highly correlated with the observed outcomes ($r=0.83$, $p=3.3\times10^{-13}$, $n=47$), and the average absolute difference between the predicted and the observed age is 5.3 years.
Figure 9:
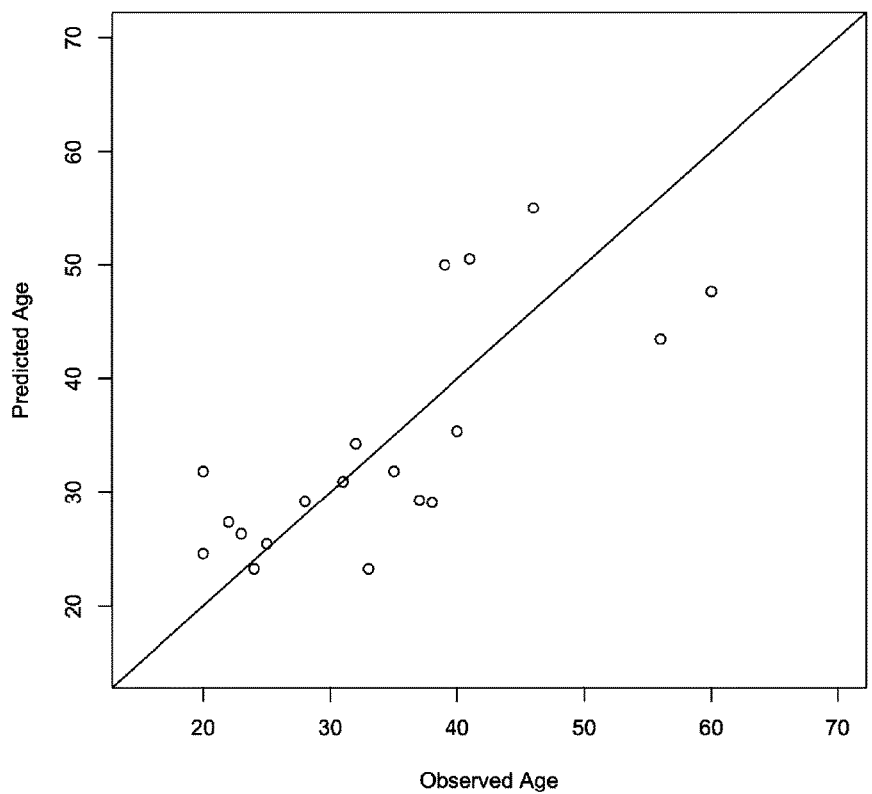
FIG. 9 illustrates predicted versus observed age of all female subjects using a leave-one-out model. A multivariate regression model was fit on all but one sample and its predicted age (y-axis) was related to the truly observed age of the left out sample (x-axis). The predicted values are highly correlated with the observed outcomes ($r=0.75$, $p=2.4\times10^{-4}$, $n=19$), and the average absolute difference between the predicted and the observed age is 6.2 years.
Figure 10:
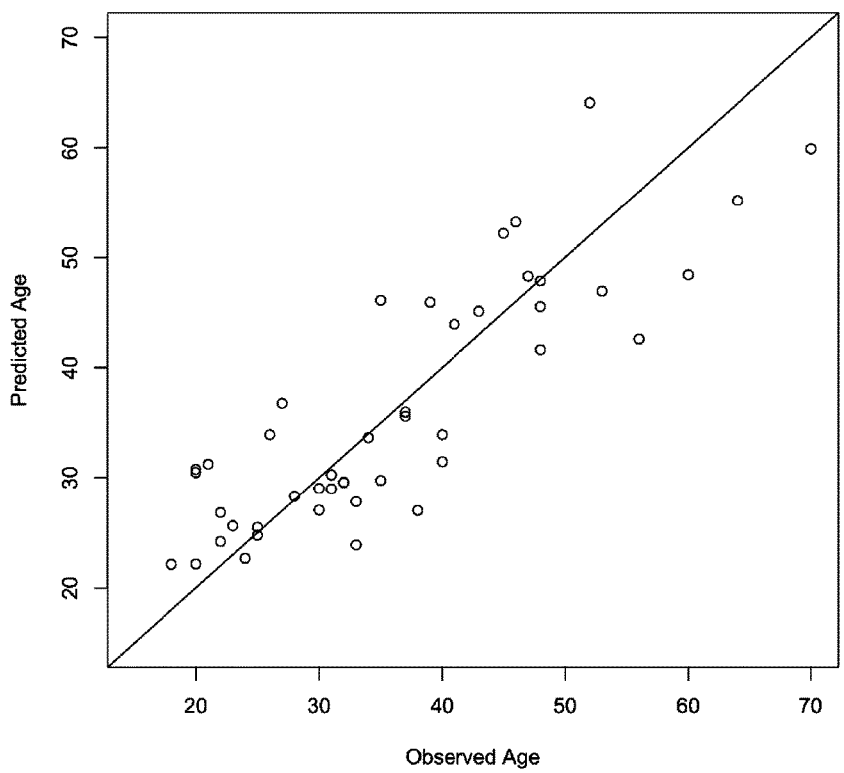
FIG. 10 illustrates predicted versus observed age of all non-twin subjects using a leave-one-out model. A multivariate regression model was fit on all but one sample and its predicted age (y-axis) was related to the truly observed age of the left out sample (x-axis). The predicted values are highly correlated with the observed outcomes ($r=0.85$, $p=1.701\times10^{-13}$, $n=45$) and the average absolute difference between the predicted and the observed age is 5.3 years.
Figure 11:
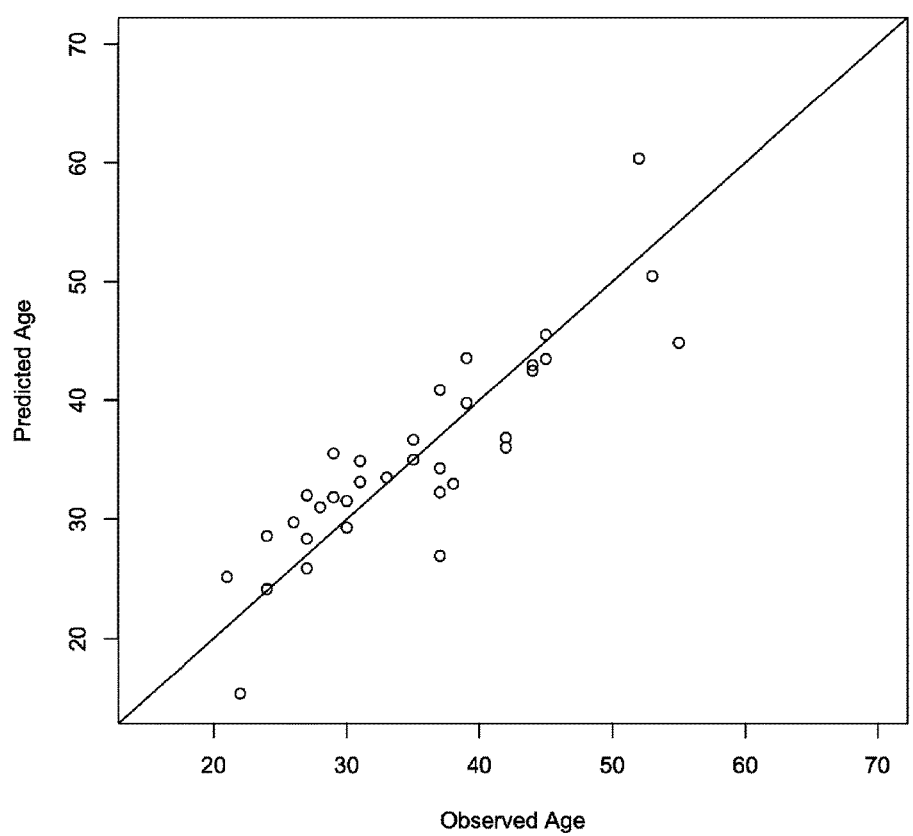
FIG. 11 illustrates predicted versus observed age of all twin subjects using a leave-one-out model. A multivariate regression model was fit on data of previously used markers plus the methylation value at the ELN gene, on microarray data, for all but one sample and its predicted age (y-axis) was related to the truly observed age of the left out sample (x-axis). The predicted values are highly correlated with the observed outcomes ($r=0.87$, $p=2.2\times10^{-11}$, $n=34$), and the average absolute difference between the predicted and the observed age is 3.5 years.

To provide an unbiased estimate of predictive accuracy for age, we used a leave-one-out analysis where the multivariate regression model was fit on all but one subject and its prediction was related to the truly observed age of the left-out subject. The predicted values are highly correlated with the observed age in males ($r=0.83$, $p=3.3\times10^{-13}$, n=47, FIG. 8), females ($r=0.75$, $p=2.4\times10^{-4}$, n=19, FIG. 9), and in the combined sample ($r=0.83$, $p=2.2\times10^{-16}$, n=66, FIG. 3). For the male only or female only models, the average absolute differences between the predicted and the observed age (the error) are 5.3 years and 6.2 years, and for the combined sample this is 5.2 years. Even when only the male and female replication samples were used, discarding all twin data, the accuracy of the model remained at 5.3 years, and the predicted values correlated highly with the observed age ($r=0.85$, $p=1.701\times10^{-13}$, n=45, FIG. 10).

To test whether additional data points on the microarray could improve the accuracy of the model, we performed lasso penalized regression to screen for the top predictors of age (see, e.g. Tibshirani R (1997) The lasso method for variable selection in the Cox model. *Stat Med* 16: 385-395; Wu T T, et al. (2009) Genome-wide association analysis by lasso penalized logistic regression. *Bioinformatics* 25: 714-721). The top five predictors were tested, and only three were found to contribute significantly to the regression model: Edaradd, NPTX2, and ELN. The first two predictors were already part of the model. Using the microarray methylation data for these two genes, the average error is 4.7 years ($r=0.77$, $p=1.029\times10-07$, n=34). Adding the ELN methylation data improved the accuracy of our model, reducing the average error to 3.5 years ($r=0.87$, $p=2.2\times10-11$, n=34, FIG. S5). Results were nearly identical when all twin samples were treated as unrelated individuals, and when averaged values for each pair were used. The distribution of methylation values for ELN was considered too narrow for further validation using pyrosequencing or MassArray analysis.

DISCUSSION AND CHARACTERIZATION OF EXPERIMENTAL DATA

In this high density, genome-wide screening of CpG methylation of twins, we identified 88 CpG sites near 80 genes for which the percent methylation in saliva is significantly correlated with age. These are highly enriched for genes known to influence age-related diseases—mainly cardiovascular and neurological disease. Ten of these 88 CpG sites were shown earlier to be correlated with age in whole blood and in isolated CD4+ and CD14+ cells as well (see, e.g. Rakyan V K, et al. (2010) Human aging-associated DNA hypermethylation occurs preferentially at bivalent chromatin domains. *Genome Res* 20: 434-439). We validated three genes in a sample of unrelated males and females, which confirmed our findings in these replicate samples. Remarkably, the methylation values for the validated genes are linear with age over a span of five decades and in three separate sample sets. Based on this observation, we were able to build a model that can predict the age of a subject based on the methylation status of just two cytosines in the genome, explaining 73% of the variance in age.

Of the validated genes, Neuronal Pentraxin II (NPTX2) methylation has been shown to be upregulated in pancreatic cancer (see, e.g. Park J K, et al. (2007) Quantitative analysis of NPTX2 hypermethylation is a promising molecular diagnostic marker for pancreatic cancer. *Pancreas* 35: e9-15), and its expression is increased in Parkinson's disease (see, e.g. Moran L B, et al. (2008) Neuronal pentraxin II is highly upregulated in Parkinson's disease and a novel component of Lewy bodies. *Acta Neuropathol* 115: 471-478). Its methylation status was recently shown to be correlated with age in blood as well (see, e.g. Rakyan V K, et al. (2010) Human aging-associated DNA hypermethylation occurs preferentially at bivalent chromatin domains. *Genome Res* 20: 434-439). Mutations in the Edar associated death domain (Edaradd) can cause loss of hair, sweat glands, and teeth (see, e.g. Yan M, et al. (2002) Identification of a novel death domain-containing adaptor molecule for ectodysplasin-A receptor that is mutated in crinkled mice. *Curr Biol* 12: 409-413), and it can reduce the speed of wound healing (see, e.g. Langton A K, et al. (2008) An extended epidermal response heals cutaneous wounds in the absence of a hair follicle stem cell contribution. *J Invest Dermatol* 128: 1311-1318). Further research should focus on their role in aging, and age-related diseases.

The lack of epigenetic drift within each monozygotic pair contrasts with a previous study (see, e.g. Fraga M F, et al. (2005) Epigenetic differences arise during the lifetime of monozygotic twins. *Proc Natl Acad Sci USA* 102: 10604-10609). The main difference between the two studies is that we focused on CpG sites close to functional gene transcription start sites whereas Fraga and colleagues investigated random sites, most of which were located in non-functional repeated sequences (e.g., Alu repeats). This suggests that while drift may occur randomly with age in non-coding, repeat-rich DNA regions, the critical regulatory portions of the genome remain under strict epigenetic control throughout life.

Our regression model (FIG. 3) could be applied in a variety of contexts. For instance, our ability to predict an individual's age to an average accuracy of 5.2 years could be used by forensic scientists to estimate a person's age based on a biological sample alone, once the model has been tested in various biological tissues. The model is also relevant to healthcare applications. Previously, significant DNA methylation differences were shown to be associated with specific age-related disorders, for example in comparisons between the brains of people diagnosed with late-onset Alzheimer's disease and brains from controls (see, e.g. Wang S C, et al. (2008) Age-specific epigenetic drift in late-onset Alzheimer's disease. *PLoS One* 3: e2698). The identification of specific epigenetic patterns highly correlated with age has the potential to influence our understanding of aging in health and disease. Specifically, it could lead to clinical interventions that are tailored to patients based on their "bio-age"—a result of the interaction of genes, environment, and time—rather than their chronological age. Future investigations should focus on phenotype and disease history of those subjects whose predicted age vary widely from their actual age. Furthermore, these findings could pave the way for interventions based on specific epigenetic marks associated with disease, as is already the case in cancer treatment (see, e.g. Marks P A, et al. (2007) Dimethyl sulfoxide to vorinostat: development of this histone deacetylase inhibitor as an anticancer drug. *Nat Biotechnol* 25: 84-90).

TABLE 1

ILLUSTRATIVE SEQUENCES IN THE Edaradd, Tom1L1, NPXT2 and ELN GENES

Edaradd:

(SEQ ID NO: 5)
F: GGTAGATTAAGAGGAAGTTTATTTTTTTAT (SEQ ID NO: 6)
R: AATACCTCTCCCCATCTATTTAATC (SEQ ID NO: 1)
TTGTATGGGAACTCTGGTGAATGCGAATCA
TTTTTAAATTACTTTTTTTGTAAAGTGCAA
AACAACAATAGCACCCATTTGCGTCATACT
TTATAGTTCGCAAAGCACATGGGAAAAATA
AAGGTAATGATGGGGATCGTTGCAATTCAT
AGGAAAGGAGGCACGAGGAAATGAAAATGA
AAGGGAGTAATAACTACGTAACTAGTCAAT
CTTCCTTAAAAAAAAAAACCCTTAAAATAT
ACCACCATCTTCTATTTGATATAATGCAGA
ATGGGAATGATAAAAACATGAATTACATTT
CAGAGTTTCAAAAAGCAAACCAGCTTTATA
GCAATGCTTGAGGTTGGGCTGCTAACAAGC
TCACTCAACTAGTGTTTCCTGACGGCCAAC
GTCAGAATAATTCCATCTCCATGAGAAGTA
CAGAAAGAACCACAAACCAAACCTCCAAAT
TGATTCTAAGATAAAATACCCTTAAAAAAA
ATTTCCCTTCCTATCCGGGCGGCAGACCAA
GAGGAAGTTTATCCTCCCACCTACAAATTC
TCCCAGAGAGCTTCATCTAGAAGGTTTGAC
TCTGGCCAGACAACCAGCGAGCATCTTCTC
GCAATCTGTTGCTTCTTCCATGGCAAACTC
CAGAGAATTAAGAAGCCAAACTCAACATCG
CCATGGGCCTCAGGACGACTAAACAGATGG
GGAGAGGCACTGGCAGACCAAGAGGAAGTT
TATCCTCCCACCTACAAATTCCCCAGAGAG
CTTTCATCTAGAAGGTTTGACTCTGGCCAG
ACAACCAGCGAGCATCTTCTCGCAATCTGT
TGCTTCTTCCATGGCAAACTCCAGAGAATT
AAGAAGCCAAACTCAACATCGCCATGGGCC
TCAGGACGACTAAACAGATGGGGAGAGGCA
CTAAAGCTCCTGGTCACCAAGAGGGTATGT
AGGCATTTGCTGTCTTCCTGGATTTCTCAG
AGCTGAGTTTTTAGCCAGAGGTTGCTTATT
TACGATAATTCTTGGATATATTATACACTA
AATACTATTATTATCTTTTTCGACCCGACT
TTTATCTTTCTGTTCTTATGTGTGAAGGCA
GAGAAAGATTATTTAGAGCTCTTCAAAGAT
TCCTATTTAATTTAAAATGCCTGTCGCCTT

TABLE 1-continued

ILLUSTRATIVE SEQUENCES IN THE Edaradd, Tom1L1, NPXT2 and ELN GENES

CCTATAATAGGCTTATGATGGATGATAGCT
TTAGTTAAAATGTAGCAATCTTAAATATAT
T

Tom1L1:

(SEQ ID NO: 7)
F: TTAATTTATTGTAGAATTTT

(SEQ ID NO: 8)
R: AAACCTCCTCTTCTAATCTATAAAAC

(SEQ ID NO: 9)
Sequencing primer: <u>ATAAAATATTTAAACCTCCA</u>

(SEQ ID NO: 2)
CTCCTCGCGGGTCCCGCAGGGCGCGCTGCA
GGTGCGCTGGGCGTCCCGAAGCCCCGCCCT
CGCGTCCCTGCCCCGCGCCCAGCTCCTCAC
GCTCGGTGCCCGCGCCCCGCAGCGGCAGCG
CAGAACGCACCGCCTCTGCCAGAGCCCGGG
AAGCGCTCGGGCGAAGAGGAGGAGCCAAGG
GTACCGAGCGGGTGGAGTCGGGAGCCGGAG
AGCGGTGGAGGCGGATTTCCTGGGCCCGGC
CCTCTGGCGCTACCATGGCGTTTGGCAAGA
GTCACCGGGATCCCTACGCGACCTCCGTGG
GCCACCTCATAGGTAAGGAGGCGCGGGGAG
AGACGCCCAGGCAGGCAGGGGACCGTGGGA
TCCTTTCCTGCTTGATCCATTCTCGGCCTG
CAGAGGACGGAGTTAGTCCAACTTGAAAAA
ATTATTCCCCTCCCCCCGCAACTTTCCCAA
GGCACCCGCATTCCACCCGGCCCCTTTCG
TCGTTTCCTTCTTGGC**CAACTCACTGTAGA
ACCTC**AGTCCTCAAAAATGTACCTTCCTTT
CGATGCCGCCTGGGGAGTGGAACCAAACAG
GTGAACCGCGGGAGTCAGGC**ATGGAGTGTT
TGGGCCTCCA**CGAGGAGACACCAGAAACTT
CTCGGTAGGGGAAGTTATTCCTAAAGGCAC
ATTCTCCAGGGCA*C*GGTATTGTTATGCCCG
TTTTACAGATCAGAAGAGGAGGCTCTGGGA
GACTAAGTGATGTGGCCTTACTGTGAGGGG
CAGGTCTCCCCAAACCAGTTTTCTCTAGTG
CCAAGCTTATACAACCTGGATTACTTTTCT
GGGTAAACAAAGAGAATGAAAATGCTTGGC
ATTGGAGTGAAGAGGAGGGGAACATAGGAG
CCATCTGGGGCCACGGAGGTCTCTCGCAGG
CCACTAGGGACTACACCAGCATCCACCTAA
ATGATTTCTCTCTCCTCCGGATGTACCTTG
CATGATGTATGTAGAAGCCAGTGATTGGAC
TCCTACCAGCACCAGCTCACTGCTCCTTCT
TTTCCCTGATTCCTCCCTTGGGAATTGGGT
GTGGCACGAGTGCATATTAATGCCAGGCAA
AGTGTGATGATGTCAGGAACTTAGTGGGGT
GATGAAATCGTGAGAACCTAGTAGTTGTAG
TAAAGAGGCCCAGATTTGGAAAATTTAGAT
CACAGCTCTACTAACTGCTGTGACACCGAA
CACACCACTTAAACAGAACCT

NP TX2:

(SEQ ID NO: 10)
F: TAGTTTAAGAAAGGG

(SEQ ID NO: 11)
R: AACTATCCTAAACCCCAAC

(SEQ ID NO: 12)
Sequencing primer: <u>ACAAAAAACTTCTACCC</u>

(SEQ ID NO: 3)
CTCCTTCCCGCCTCGAGAGTGAGGTGGCCG
GGCCTTGACGAGAAGGCCCACGCCTGCCGC
GGGGGTGGCTCGCGATGGCAGTCGGGGTTC
GAGTCCCGCCTGGGGGCTGCTCCTGCTGG
AGAAAACGCCTCCCTGAGGGCGGCGGCAAA
CGCGCAGCGAGGCCCCGTGCCGCGCCAGAA
GCCACCCTGAGAAAGGGGCACCGGGACACC
GAGGGGTTCCCACTTTCTCCTCAGCCTGTG

ACGCCCGCGTCCTCGGGTGGGTTCGAGGGG
CGCCTGGGCACGGCCAGCCGAGGCTCTCGA
GAGCCCCAGTGTCGTTTTCCACCTCAGGCC
TCCTTTCCTGAGGCAGAGCCCGGGACCTCG
CGCTCTCGCCTCAGGCTCCGGCCCACGCTC
CCGCCCGGCCGCCAGGCGCGCAACGGAAAG
CGCCCCCGCCCCGCCCCGCTCCGCCCACTG
CGTGACGCGCACCCGGCCGAGCCAATCAGA
GCTCGTGGCGCGCGCCCCACACGCCGGCCC
CCTCCGCCCCTCAGCTTAAGAAAGGGCGCG
CGGACCCGGCAGGCCAGAGTGCCGAGCAGC
GCGGTGGGTGCGGCTGTGAGACGG*CAGGAG
ACTTCTGCCCC*GC*GG*T*GCA*CGC*GACCCT*CG*
AGACGACAG*CGC*GGCTACTGCCAGCAGCGA
AGG*CGC*CTCC*CGC*GGAG*CGC*CCCGACGG*CG*
CC*CGC*T*CGC*CCATGC*CG*AGCTGAGCG*CGGC*
AG*CGGCGG*CGGGATGCTGG*CG*CTGCTGGCC
*GC*CAGC*GT*GG*CGC*TCGC*CG*TGGCC**GCTGGG
GCCCAGGACAGCC**CGGCGCCCGGTAGCCGC
TTCGTGTGCACGGCACTGCCCCCAGAGGCG
GTGCACGCCGGCTGCCCGCTGCCCGCGATG
CCCATGCAGGGCGGCGCGCAGAGTCCCGAG
GAGGAGCTGAGGGCCGCGGTGCTGCAGCTG
CGCGAGACCGTCGTGCAGCAGAAGGAGACG
CTGGGCGCGCAGCGCGAGGCCATCCGCGAG
CTCACGGGCAAGCTAGCGCGCTGCGAGGGG
CTGGCGGGCGGCAAGGCGCGCGGCGCGGGG
GCCACGGGCAAGGACACTATGGGCGACCTG
CCGCGGGACCCCGGCCACGTCGTGGAGCAG
CTCAGCCGCTCGCTGCAGACCCTCAAGGAC
CGCCTGGAGAGCCTCGAGGTAGCGGCCCGC
GGGGAGCGCGGGGGACCTGGAATGGGGACG
CTCCCGAGTCGGGGCGGAAG

ELN
The locus measured for the Elastin (ELN) gene is
cg05822532. The actual CpG site measured is in
underlined here:

(SEQ ID NO: 4)
CCTCCCTCTTTCCCTCACAGCCGACGAGGCA
ACAATTAGGCTTTGGGGATAAAACGAGGTGC
GGAGAGCGGGCTGGGGCATTTCTCCCCGAGA
TGGCGGGTCTGA<u>CG</u>GCGGCGGCCCCGCGGCC
CGGAGTCCTCCTGCTCCTGCTGTCCATCCTC
CACCCCTCTCGGCCTGGAGGTAAGGACCCCT
CGCCCCTGTCCCCAGCGCTGCCCACA

In this table, illustrative primer sequences are shown in bold. Note that the sequence shown is the genomic DNA sequence, while the primer sequences are designed to bind to bisulfite converted DNA. Hence the fact that the given primer sequences do not align exactly with the genomic sequences shown. Sequencing primers are in bold and <u>underlined</u>. Certain CpG loci correlated with age <u>underlined</u>. Additional CpGs that are assayed in the same experiment and can be correlated with age are in *italics*.
The exact location in the March 2006 build of the human genome (NCBI36/hg18) is chromosome 7, pos 73080467.

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

The invention claimed is:

1. A method of obtaining information useful to determine an age of an individual, the method comprising the steps of:
   (a) obtaining genomic DNA from white blood cells or epithelial cells derived from the individual;
   (b) observing cytosine methylation of cg12799895 and cg09809672 CG loci designations in the genomic DNA;
   (c) further observing cytosine methylation of at least two CG loci in the genomic DNA selected from the group consisting of CG locus designation: cg14456683, cg05508084, cg00399483, cg02008154, cg20366906, cg20134215, cg13614181, cg23563234, cg00911351, cg15425280, cg06156376, cg19831077, cg20616414, cg24646414, cg17241310, cg10031651, cg06908778, cg14614211, cg15201635, cg06760035, cg13603171, cg13282837, cg13547237, cg17589341, cg03440846, cg08909157, cg11136562 and cg16464322, wherein said observing comprises performing a bisulfate conversion process on the genomic DNA so that cytosine residues in the genomic DNA are transformed to uracil, while 5-methylcytosine residues in the genomic DNA are not transformed to uracil;
   (c) comparing the CG locus methylation observed in (b) to the CG locus methylation observed in genomic DNA from white blood cells or epithelial cells derived from a group of individuals of known ages; and
   (d) correlating the CG locus methylation observed in (b) with the CG locus methylation and known ages in the group of individuals;
   so that information useful to determine the age of the individual is obtained.

2. The method of claim 1, further comprising correlating cytosine methylation observed in the CG loci with a predicted chronological age of the individual, wherein a multivariate regression analysis is used to correlate cytosine methylation observed with the predicted chronological age of the individual.

3. The method of claim 1, wherein the genomic DNA is hybridized to a complimentary sequence disposed on a microarray.

4. The method of claim 1, wherein the genomic DNA is amplified by a polymerase chain reaction process.

5. The method of claim 1, wherein the individual's identity is unknown.

6. The method of claim 1, further comprising performing a DNA fingerprinting analysis on the genomic DNA.

7. The method of claim 1, further comprising using the information in a forensic investigation.

8. The method of claim 1, further comprising comparing the predicted age of the individual with the actual chronological age of the individual, wherein the comparison comprises a diagnostic procedure for an age associated pathology.

9. The method of claim 2, wherein a least squares regression analysis is used to correlate the pattern of cytosine methylation observed with the predicted age of the individual.

10. A method of obtaining information useful to determine an age of an individual, the method comprising the steps of:
   (a) obtaining genomic DNA from leukocytes or epithelial cells derived from the individual;
   (b) observing cytosine methylation of cg12799895 and cg09809672 CG loci designations in the genomic DNA;
   (c) further observing cytosine methylation of at least two CG loci in the genomic DNA selected from the group consisting of CG locus designation: cg14456683, cg05508084, cg00399483, cg02008154, cg20366906, cg20134215, cg13614181, cg23563234, cg00911351, cg15425280, cg06156376, cg19831077, cg20616414, cg24646414, cg17241310, cg10031651, cg06908778, cg14614211, cg15201635, cg06760035, cg13603171, cg13282837, cg13547237, cg17589341, cg03440846, cg08909157, cg11136562 and cg16464322, wherein said observing comprises performing a bisulfate conversion process on the genomic DNA so that cytosine residues in the genomic DNA are transformed to uracil, while 5-methylcytosine residues in the genomic DNA are not transformed to uracil;

(c) comparing the CG locus methylation observed in (b) to the CG locus methylation observed in genomic DNA from leukocytes or buccal epithelial cells derived from a group of individuals of known ages; and (d) correlating the CG locus methylation observed in (b) with the CG locus methylation and known ages in the group of individuals;

so that information useful to determine the age of the individual is obtained.

11. The method of claim 10, wherein the cells are obtained from saliva from the individual.

12. The method of claim 10, wherein genomic DNA from leukocytes is obtained.

13. The method of claim 10, wherein genomic DNA from buccal epithelial cells is obtained.

14. The method of claim 10, wherein the genomic DNA is hybridized to a complimentary sequence disposed on a microarray.

15. The method of claim 1, further comprising observing cytosine methylation of at least two CG loci in the genomic DNA selected from the group consisting of CG locus designation: cg27553955, cg21296230, cg03734874, cg07621046, cg00107187, cg07533148, cg03975694, cg06291867, cg24826867, cg06092815, cg24199834, cg04528819, cg13434842, cg25044651, cg02994956, cg27389185, cg14826456, cg12111714, cg12457773, cg11981599, cg06572160, cg08668790, cg12782180, cg13921352cg00201234, cg21992250, cg27409364, cg02154186, cg20616414, cg10235817, cg23290344, cg02844545, cg25511429, cg19246110, cg20792062, cg02228185, cg01293143, cg07408456, cg08468689, cg01820374, cg19761273, cg08872742, cg18328933, cg15784615 and cg23282949.

16. The method of claim 15, wherein cytosine methylation of at least forty CG loci in the genomic DNA are observed.

17. The method of claim 10, further comprising observing cytosine methylation of at least two CG loci in the genomic DNA selected from the group consisting of CG locus designation: cg27553955, cg21296230, cg03734874, cg07621046, cg00107187, cg07533148, cg03975694, cg06291867, cg24826867, cg06092815, cg24199834, cg04528819, cg13434842, cg25044651, cg02994956, cg27389185, cg14826456, cg12111714, cg12457773, cg11981599, cg06572160, cg08668790, cg12782180, cg13921352cg00201234, cg21992250, cg27409364, cg02154186, cg20616414, cg10235817, cg23290344, cg02844545, cg25511429, cg19246110, cg20792062, cg02228185, cg01293143, cg07408456, cg08468689, cg01820374, cg19761273, cg08872742, cg18328933, cg15784615 and cg23282949.

18. The method of claim 17, wherein cytosine methylation of at least forty CG loci in the genomic DNA are observed.

* * * * *

SEQUENCE LISTING

<160> NUMBER OF SEQ ID NOS: 12

<210> SEQ ID NO 1
<211> LENGTH: 1201
<212> TYPE: DNA
<213> ORGANISM: Homo sapiens

<400> SEQUENCE: 1

| | | | | | |
|---|---|---|---|---|---|
| ttgtatggga | actctggtga | atgcgaatca | tttttaaatt | acttttttg | taaagtgcaa | 60 |
| aacaacaata | gcacccattt | gcgtcatact | ttatagttcg | caaagcacat | gggaaaaata | 120 |
| aaggtaatga | tggggatcgt | tgcaattcat | aggaaaggag | gcacgaggaa | atgaaaatga | 180 |
| aagggagtaa | taactacgta | actagtcaat | cttccttaaa | aaaaaaaacc | cttaaaatat | 240 |
| accaccatct | tctatttgat | ataatgcaga | atgggaatga | taaaaacatg | aattacattt | 300 |
| cagagtttca | aaaagcaaac | cagctttata | gcaatgcttg | aggttgggct | gctaacaagc | 360 |
| tcactcaact | agtgtttcct | gacggccaac | gtcagaataa | ttccatctcc | atgagaagta | 420 |
| cagaaagaac | cacaaaccaa | acctccaaat | tgattctaag | ataaaatacc | cttaaaaaaa | 480 |
| atttcccttc | ctatccgggc | ggcagaccaa | gaggaagttt | atcctcccac | ctacaaattc | 540 |
| cccagagagc | tttcatctag | aaggtttgac | tctggccaga | caaccagcga | gcatcttctc | 600 |
| gcaatctgtt | gcttcttcca | tggcaaactc | cagagaatta | agaagccaaa | ctcaacatcg | 660 |
| ccatgggcct | caggacgact | aaacagatgg | ggagaggcac | tggcagacca | agaggaagtt | 720 |
| tatcctccca | cctacaaatt | ccccagagag | ctttcatcta | gaaggtttga | ctctggccag | 780 |
| acaaccagcg | agcatcttct | cgcaatctgt | tgcttcttcc | atggcaaact | ccagagaatt | 840 |
| aagaagccaa | actcaacatc | gccatgggcc | tcaggacgac | taaacagatg | gggagaggca | 900 |
| ctaaagctcc | tggtcaccaa | gagggtatgt | aggcatttgc | tgtcttcctg | gatttctcag | 960 |
| agctgagttt | ttagccagag | gttgcttatt | tacgataatt | cttggatata | ttatacacta | 1020 |
| aatactatta | ttatcttttt | cgacccgact | tttatctttc | tgttcttatg | tgtgaaggca | 1080 |
| gagaaagatt | atttagagct | cttcaaagat | tcctatttaa | tttaaaatgc | ctgtcgcctt | 1140 |
| cctataatag | gcttatgatg | gatgatagct | ttagttaaaa | tgtagcaatc | ttaaatatat | 1200 |
| t | | | | | | 1201 |

<210> SEQ ID NO 2
<211> LENGTH: 1221
<212> TYPE: DNA
<213> ORGANISM: Homo sapiens

<400> SEQUENCE: 2

| | | | | | |
|---|---|---|---|---|---|
| ctcctcgcgg | gtcccgcagg | gcgcgctgca | ggtgcgctgg | gcgtcccgaa | gccccgccct | 60 |
| cgcgtccctg | ccccgcgccc | agctcctcac | gctcggtgcc | cgcgccccgc | agcggcagcg | 120 |
| cagaacgcac | cgcctctgcc | agagcccggg | aagcgctcgg | gcgaagagga | ggagccaagg | 180 |
| gtaccgagcg | ggtggagtcg | ggagccggag | agcggtggag | gcggatttcc | tgggcccggc | 240 |
| cctctggcgc | taccatggcg | tttggcaaga | gtcaccggga | tccctacgcg | acctccgtgg | 300 |
| gccacctcat | aggtaaggag | gcgcggggag | agacgcccag | gcaggcaggg | gaccgtggga | 360 |
| tcctttcctg | cttgatccat | tctcggcctg | cagaggacga | agttagtcca | acttgaaaaa | 420 |
| attattcccc | tcccccgca | actttcccaa | ggcacccgca | ttccaccegg | cccccttteg | 480 |
| tcgtttcctt | cttggccaac | tcactgtaga | acctcagtcc | tcaaaatgt | accttcctt | 540 |
| cgatgccgcc | tggggagtgg | aaccaaacag | gtgaaccgcg | ggagtcaggc | atggagtgtt | 600 |

```
tgggcctcca cgaggagaca ccagaaactt ctcggtaggg gaagttattc ctaaaggcac      660
attctccagg gcacggtatt gttatgcccg ttttacagat cagaagagga ggctctggga      720
gactaagtga tgtggcctta ctgtgagggg caggtctccc caaaccagtt ttctctagtg      780
ccaagcttat acaacctgga ttacttttct gggtaaacaa agagaatgaa aatgcttggc      840
attggagtga agaggagggg aacataggag ccatctgggg ccacggaggt ctctcgcagg      900
ccactaggga ctacaccagc atccacctaa atgatttctc tctcctccgg atgtaccttg      960
catgatgtat gtagaagcca gtgattggac tcctaccagc accagctcac tgctccttct     1020
tttccctgat tcctcccttg ggaattgggt gtggcacgag tgcatattaa tgccaggcaa     1080
agtgtgatga tgtcaggaac ttagtggggt gatgaaatcg tgagaaccta gtagttgtag     1140
taaagaggcc cagatttgga aaatttagat cacagctcta ctaactgctg tgacaccgaa     1200
cacaccactt aaacagaacc t                                               1221

<210> SEQ ID NO 3
<211> LENGTH: 1221
<212> TYPE: DNA
<213> ORGANISM: Homo sapiens

<400> SEQUENCE: 3
ctccttcccg cctcgagagt gaggtggccg ggccttgacg agaaggccca cgcctgccgc       60
gggggtggct cgcgatggca gtcggggttc gagtcccgcc tgggggctg ctcctgctgg      120 agaaaacgcc tccctgaggg cggcggcaaa cgcgcagcga ggccccgtgc cgcgccagaa      180
gccaccctga gaaggggca ccgggacacc gagggggttcc cactttctcc tcagcctgtg      240
acgcccgcgt cctcgggtgg gttcgagggg cgcctgggca cggccagccg aggtctctcga     300 gagccccagt gtcgttttcc acctcaggcc tcctttcctg aggcagagcc cgggacctcg      360
cgctctcgcc tcaggctccg gcccacgctc ccgcccggcc gccaggcgcg caacggaaag      420 cgccccccgcc ccgccccgct ccgcccactg cgtgacgcgc accggccga gccaatcaga      480 gctcgtggcg cgcgccccac acgcggcc cctccgcccc tcagcttaag aaagggcgcg      540
cggacccggc aggccagagt gccgagcagc gcggtgggtg cggctgtgag acggcaggag      600
acttctgccc cgcggtgcac gcgaccctcg agacgacagc gcggctactg ccagcagcga      660
aggcgcctcc cgcggagcgc cccgacgcg cccgctcgcc catgccgagc tgagcgcggc      720
agcggcggcg ggatgctggc gctgctggcc gccagcgtgg cgctcgccgt ggccgctggg      780
gcccaggaca gcccggcgcc cggtagccgc ttcgtgtgca cggcactgcc cccagaggcg      840
gtgcacgccg gctgcccgct gcccgcgatg cccatgcagg gcggcgcgca gagtcccgag      900
gaggagctga gggccgcggt gctgcagctg cgcgagaccc tcgtgcagca gaaggagacg      960
ctgggcgcgc agcgcgaggc catccgcgag ctcacgggca agctagcgcg ctgcgagggg     1020
ctggcgggcg gcaaggcgcg cggcgcgggg gccacggcca aggacactat gggcgacctg     1080
ccgcgggacc ccggccacgt cgtggagcag ctcagccgct cgctgcagac cctcaaggac     1140
cgcctggaga gcctcgaggt agcggcccgc ggggagcgcg ggggacctgg aatggggacg     1200
ctcccgagtc gggggcggaa g                                               1221

<210> SEQ ID NO 4
<211> LENGTH: 212
<212> TYPE: DNA
<213> ORGANISM: Homo sapiens
```

<400> SEQUENCE: 4

```
cctccctctt tccctcacag ccgacgaggc aacaattagg ctttggggat aaaacgaggt      60
gcggagagcg ggctggggca tttctccccg agatggcggg tctgacggcg gcggccccgc     120
ggcccggagt cctcctgctc ctgctgtcca tcctccaccc ctctcggcct ggaggtaagg     180
accoctcgcc cctgtcccca gcgctgccca ca                                   212
```

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5

```
ggtagattaa gaggaagttt atttttttat                                       30
```

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6

```
aatacctctc cccatctatt taatc                                            25
```

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7

```
ttaatttatt gtagaatttt                                                  20
```

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8

```
aaacctcctc ttctaatcta taaaac                                           26
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9

```
ataaaatatt taaacctcca                                                  20
```

<210> SEQ ID NO 10
<211> LENGTH: 15
<212> TYPE: DNA
<213> ORGANISM: Artificial Sequence
<220> FEATURE:
<223> OTHER INFORMATION: Primer

<400> SEQUENCE: 10

```
tagtttaaga aaggg                                                             15

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
aactatccta aaccccaac                                                         19

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
acaaaaaact tctaccc                                                           17
```